(12) United States Patent
Lewis et al.

(10) Patent No.: US 7,365,834 B2
(45) Date of Patent: Apr. 29, 2008

(54) OPTICAL SYSTEM FOR DETECTING ANOMALIES AND/OR FEATURES OF SURFACES

(75) Inventors: Isabella Lewis, Boulder, CO (US); Mehdi Vaez-Iravani, Los Gatos, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 390 days.

(21) Appl. No.: 10/874,861

(22) Filed: Jun. 22, 2004

(65) Prior Publication Data

US 2005/0052644 A1 Mar. 10, 2005

Related U.S. Application Data

(60) Provisional application No. 60/482,539, filed on Jun. 24, 2003.

(51) Int. Cl.
*G01N 21/00* (2006.01)

(52) U.S. Cl. .................. 356/237.2; 356/237.4

(58) Field of Classification Search ... 356/237.2–237.5
See application file for complete search history.

(56) References Cited

U.S. PATENT DOCUMENTS

| | | | |
|---|---|---|---|
| 4,449,818 | A | 5/1984 | Yamaguchi et al. |
| 4,579,455 | A | 4/1986 | Levy et al. |
| 4,898,471 | A | 2/1990 | Vaught et al. |
| 4,974,927 | A | 12/1990 | Kimura |
| 5,192,856 | A | 3/1993 | Schaham |
| 5,251,010 | A | 10/1993 | Maltby, Jr. |
| 5,463,459 | A | 10/1995 | Morioka et al. |
| 5,479,259 | A | 12/1995 | Nakata et al. |
| 5,530,550 | A | 6/1996 | Nikoonahad et al. |
| 5,576,831 | A | 11/1996 | Nikoonahad et al. |
| 5,585,916 | A | 12/1996 | Miura et al. |

(Continued)

FOREIGN PATENT DOCUMENTS

EP 0266728 5/1998

(Continued)

OTHER PUBLICATIONS

International Search Report PCT/US2004/020483 (5 pages).*

(Continued)

*Primary Examiner*—L. G. Lauchman
(74) *Attorney, Agent, or Firm*—Davis Wright Tremaine LLP

(57) ABSTRACT

A surface inspection of the system applies a first oblique illumination beam and may also apply a second illumination beam to illuminate a surface either sequentially or simultaneously. Radiation reflected or scattered is collected by preferably three collection channels and detected by three corresponding detector arrays, although a different number of channels and detector arrays may be used. One or both illumination beams are focused to a line on the surface to be inspected and each line is imaged onto one or more detector arrays in the up to three or more detection and collection channels. Relative motion is caused between the lines and the surface inspected in a direction perpendicular to the lines, thereby increasing throughput while retaining high resolution and sensitivity. The same detection channels may be employed by detecting scattered or reflected radiation from both illumination beams. Fourier filters may be employed to filter out diffraction at one or more different spatial frequencies.

137 Claims, 15 Drawing Sheets

U.S. PATENT DOCUMENTS

| | | | |
|---|---|---|---|
| 5,644,393 A | 7/1997 | Nakamura et al. | |
| 5,719,840 A | 2/1998 | Jann | |
| 5,737,074 A | 4/1998 | Haga et al. | |
| 5,748,305 A | 5/1998 | Shimono et al. | |
| 5,864,394 A | 1/1999 | Jordan, III et al. | |
| 5,917,588 A | 6/1999 | Addiego | |
| 6,618,134 B2* | 9/2003 | Vaez-Iravani et al. | ... 356/237.4 |
| 6,639,662 B2* | 10/2003 | Vaez-Iravani et al. | ... 356/237.4 |
| 6,657,715 B2* | 12/2003 | Vaez-Iravani et al. | ... 356/237.4 |
| 6,956,644 B2* | 10/2005 | Biellak et al. | ........... 356/237.4 |
| 7,037,735 B2* | 5/2006 | Noguchi et al. | ............... 438/18 |
| 7,064,821 B2* | 6/2006 | Vaez-Iravani et al. | ... 356/237.4 |
| 7,088,443 B2* | 8/2006 | Vaez-Iravani et al. | ... 356/237.2 |
| 7,119,897 B2* | 10/2006 | Vaez-Iravani et al. | ... 356/237.4 |
| 2002/0041374 A1 | 4/2002 | Ohshima et al. | |
| 2002/0145732 A1 | 10/2002 | Vaez-Iravani et al. | |
| 2005/0219518 A1* | 10/2005 | Korngut et al. | .......... 356/237.2 |

FOREIGN PATENT DOCUMENTS

| | | |
|---|---|---|
| EP | 1 265 063 | 12/2002 |
| JP | 9015163 | 1/1997 |
| WO | 99/06823 | 2/1999 |
| WO | 00/68673 | 11/2000 |

OTHER PUBLICATIONS

ISA/EPO "International Search Report", mailed in related PCT/US98/16116, Nov. 27, 1998.

"Automatic Microcircuit and Wafer Inspection", Dr. Aaron D. Gara, Electronics Test, May 1981, pp. 60-70.

"Notification of Transmittal of the International Search Report and The Written Opinion of the International Searching Authority, or the Declaration", mailed in corresponding PCT/US2004/020483, Nov. 5, 2004.

EPO, "Office Action," mailed in related European Patent Application No. 04756129.5 on Feb. 12, 2007, 3 pages.

* cited by examiner

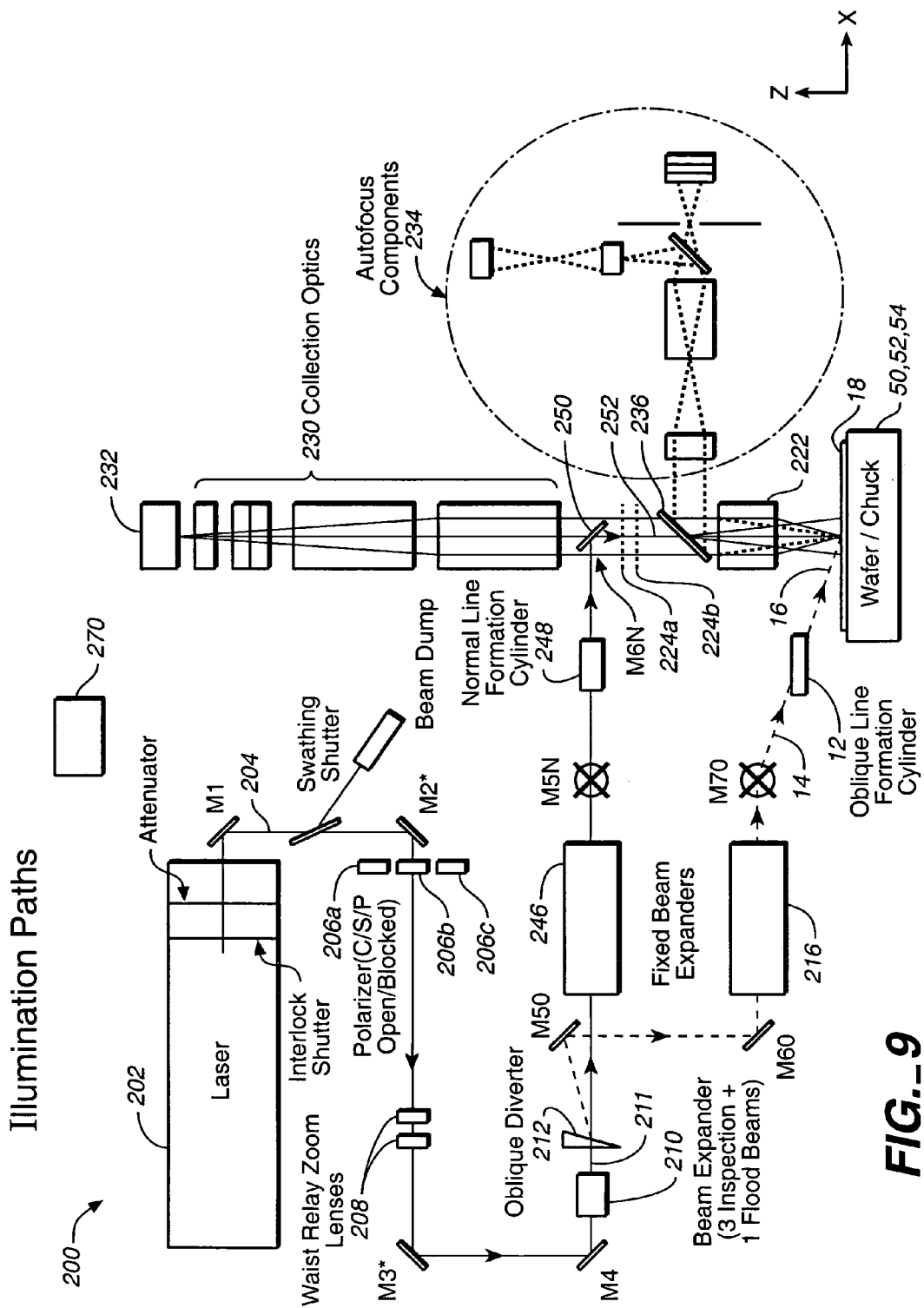
FIG._9

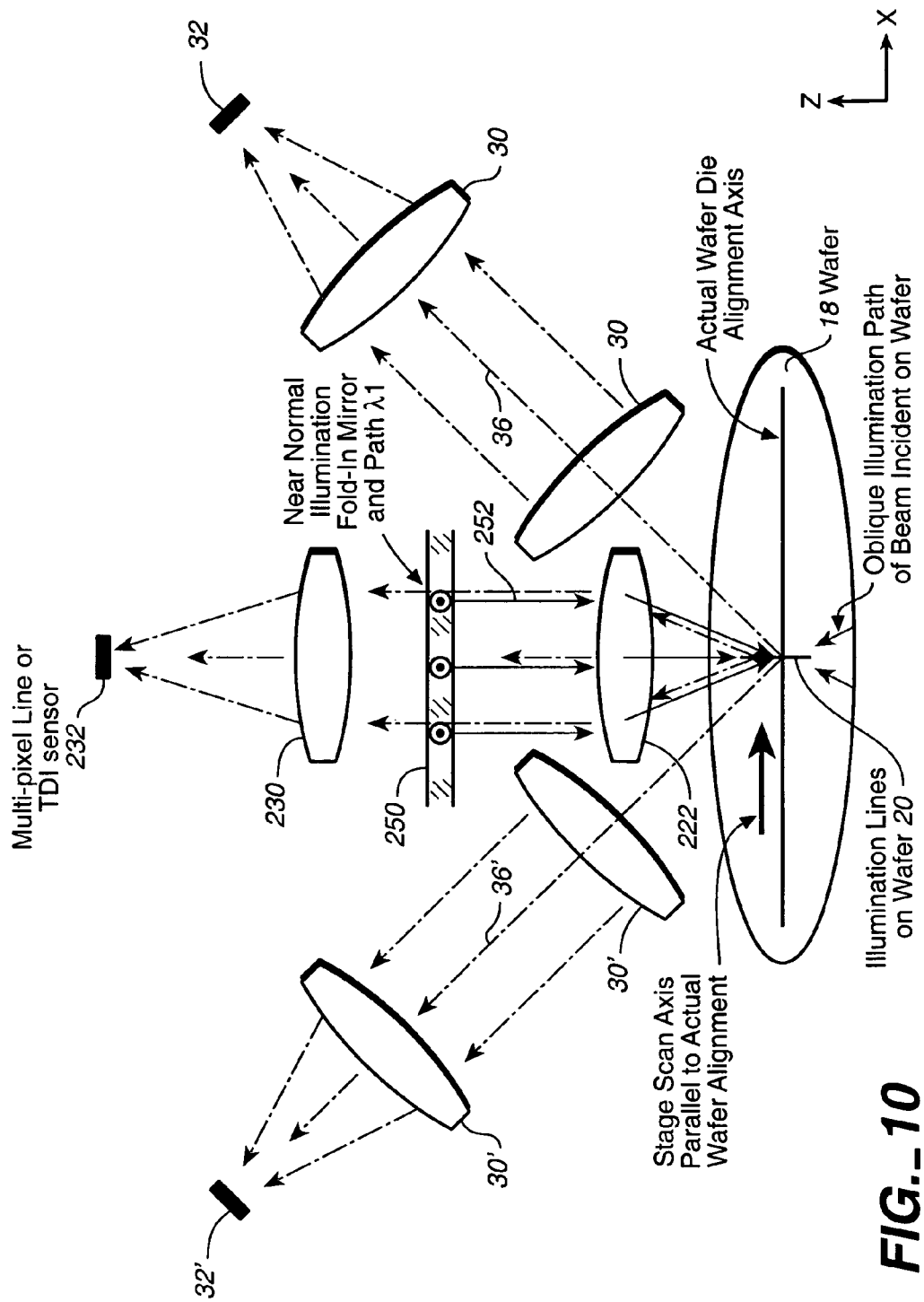
FIG._10

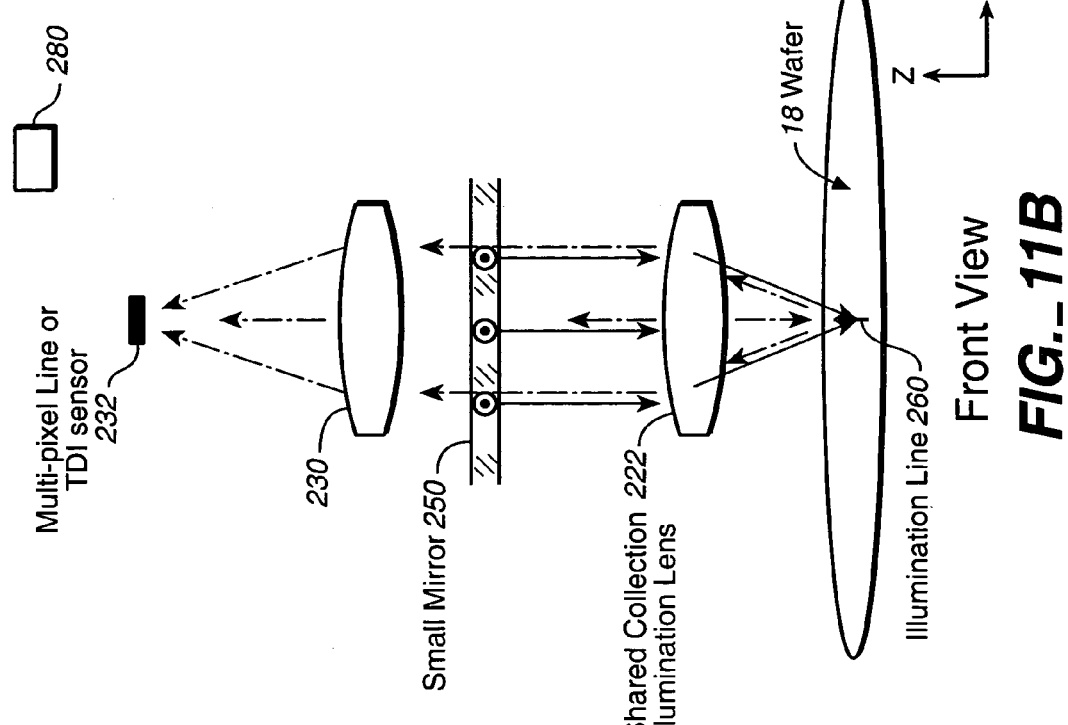
FIG._11A
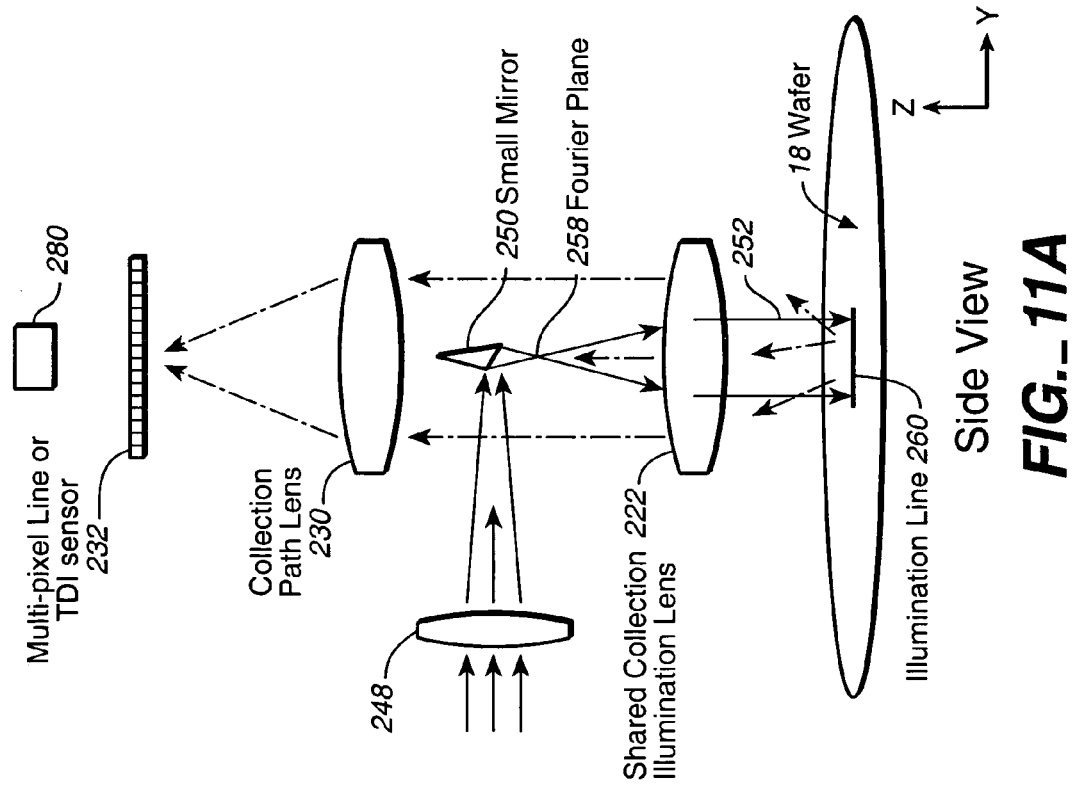
FIG._11B

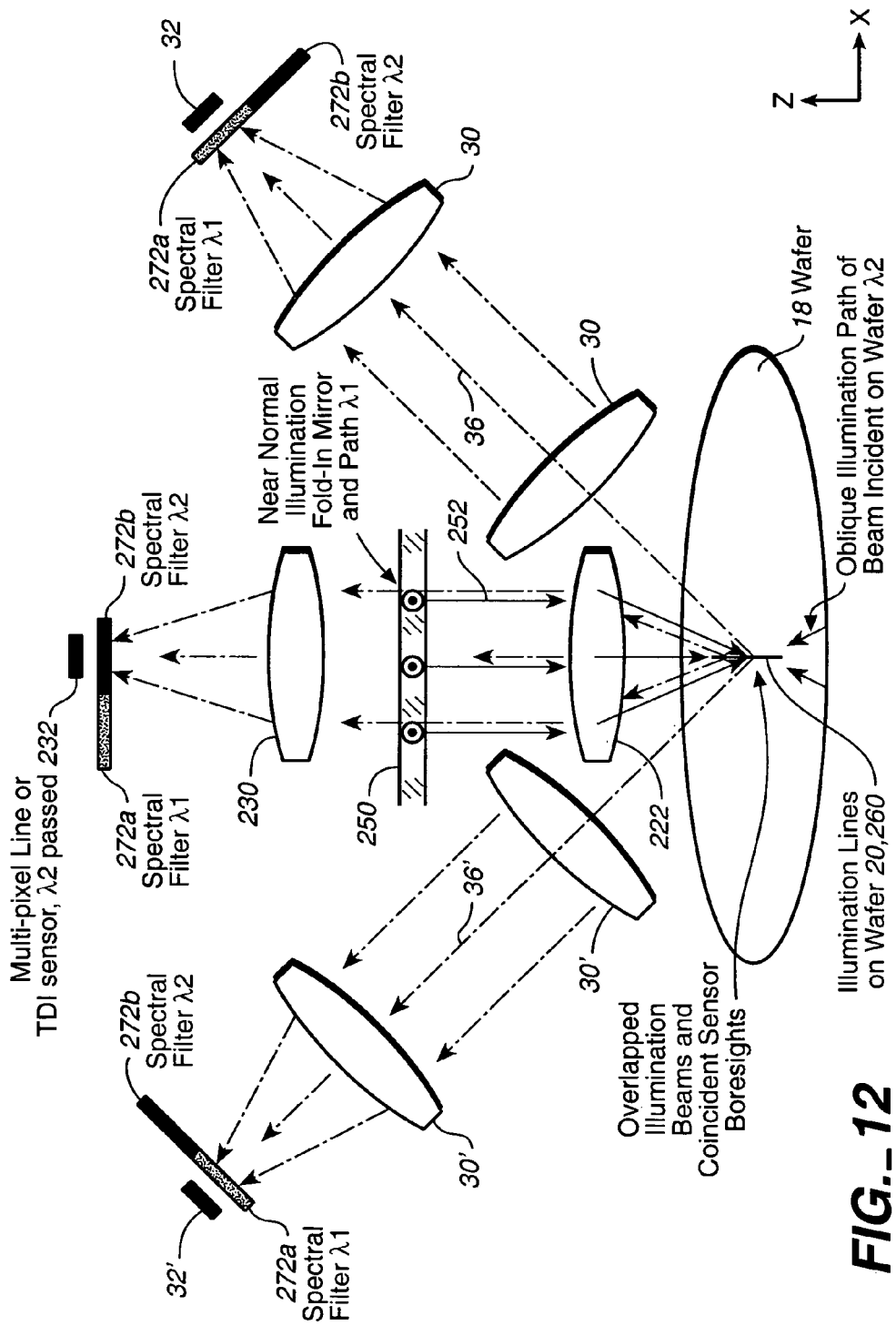
FIG._12

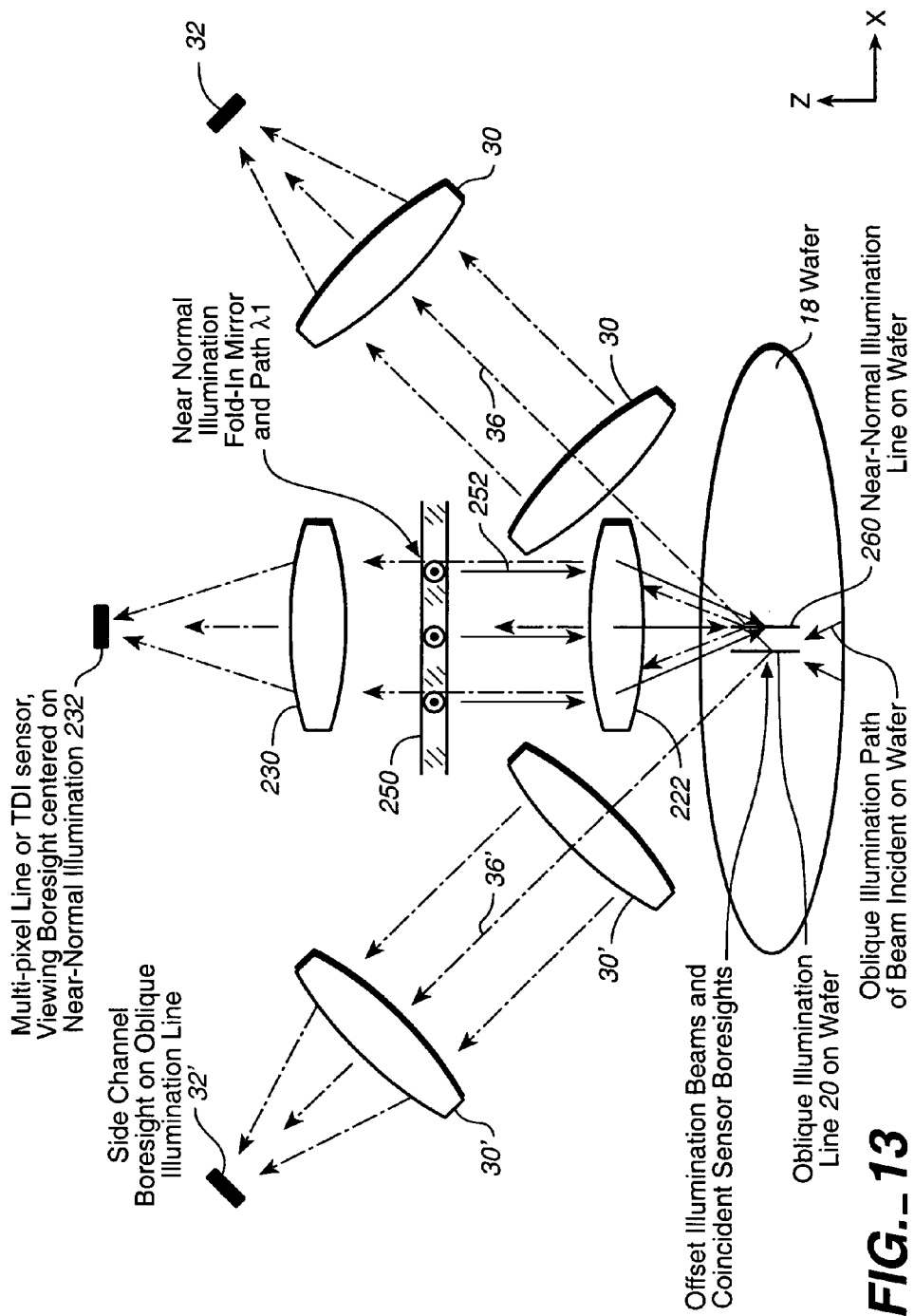
FIG._13

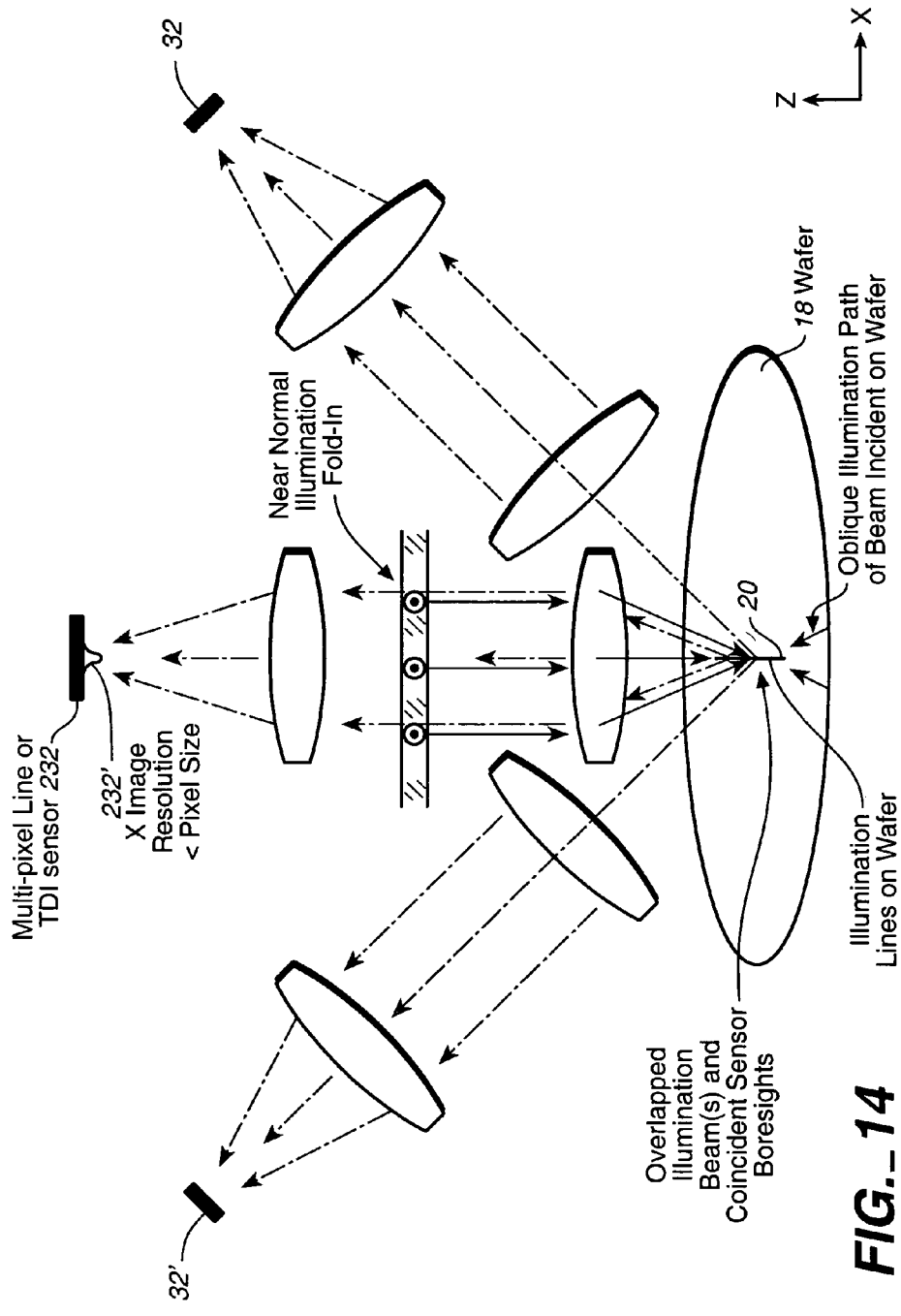
Detector and TDI with Beams on Wafer/Detector Showing X and Y Resolution-1
FIG._14

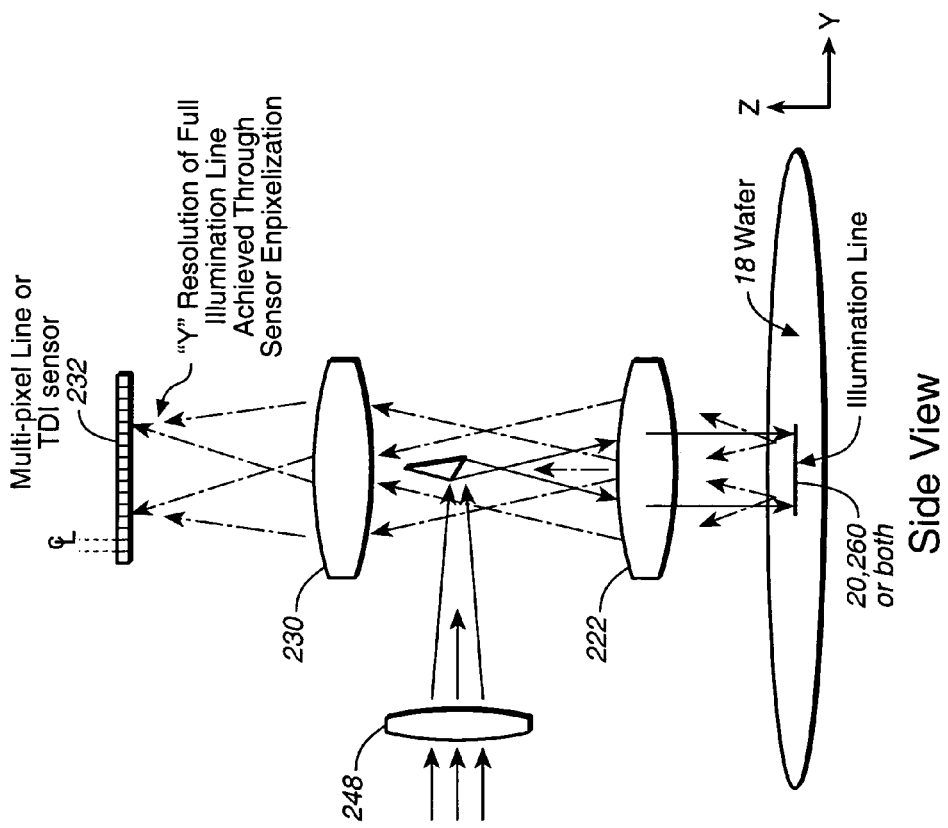
FIG._15

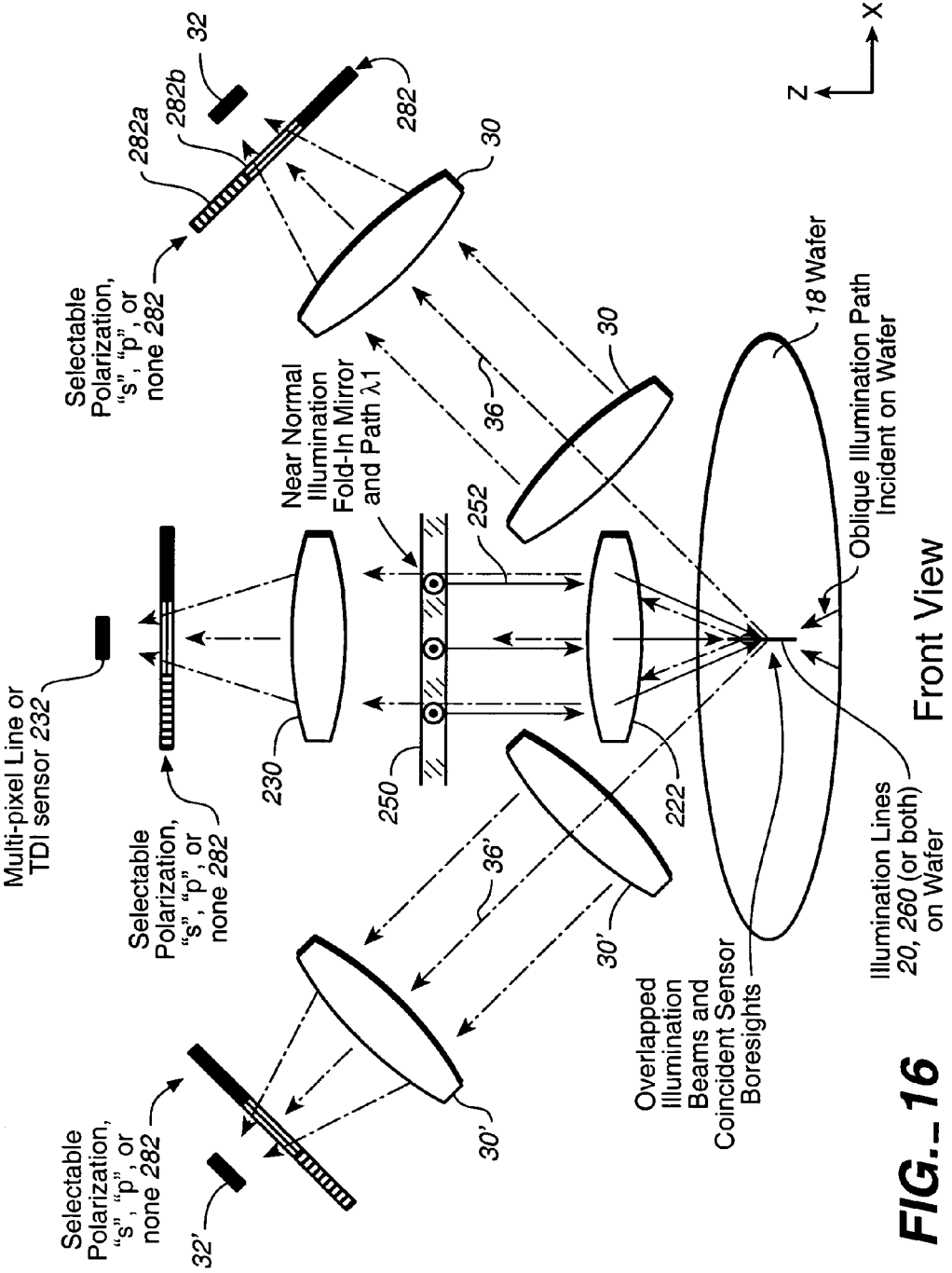
FIG._16

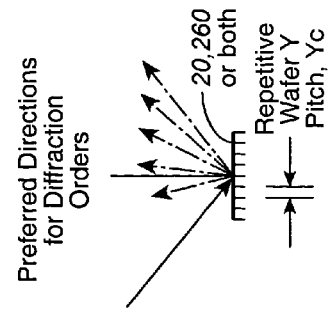
FIG._17B
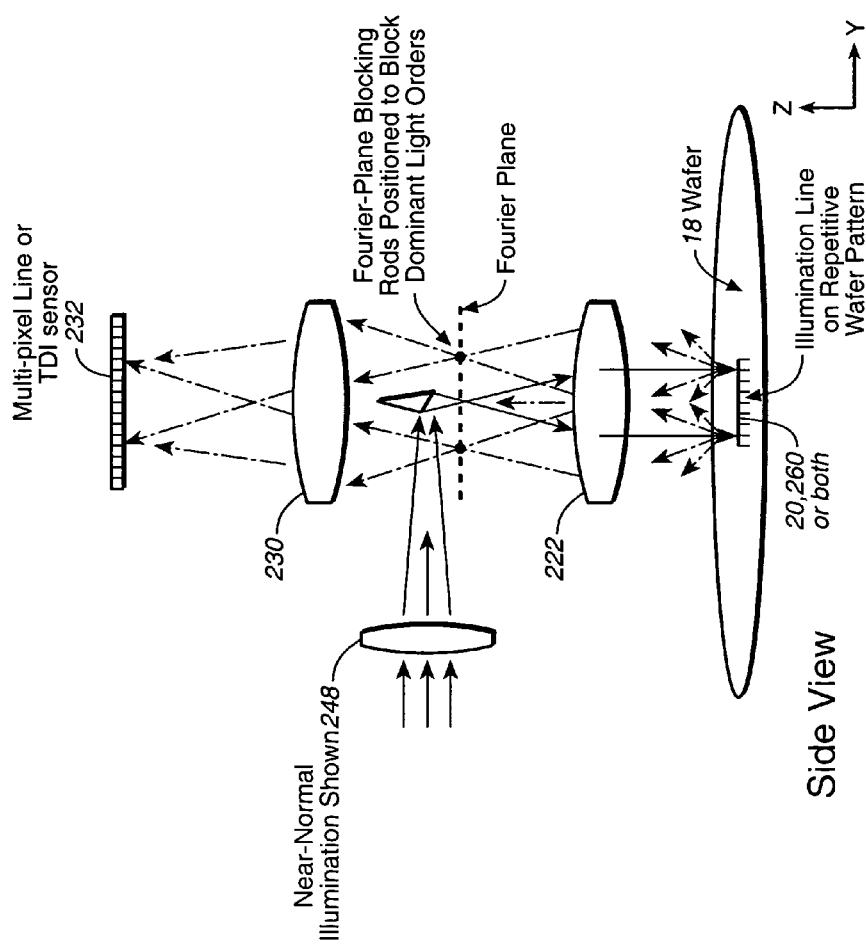
FIG._17A

_US 7,365,834 B2_

OPTICAL SYSTEM FOR DETECTING ANOMALIES AND/OR FEATURES OF SURFACES

CROSS-REFERENCE TO RELATED APPLICATION

This application claims benefit of U.S. Provisional Application Ser. No. 60/482,539 filed Jun. 24, 2003, which is related to U.S. patent application Ser. No. 08/904,892 filed Aug. 1, 1997, entitled "SYSTEM FOR DETECTING ANOMALIES AND/OR FEATURES OF A SURFACE" by Guoheng Zhao, Stanley Stokowski, and Mehdi Vaez-Iravani, herein referred to as the "Related Application". The Related Application is herein incorporated herein by reference in its entirely.

BACKGROUND OF THE INVENTION

This invention relates in general to surface inspection systems, and in particular, to an improved system for detecting anomalies and/or features of a surface.

The size of semiconductor devices fabricated on silicon wafers has been continually reduced. The shrinking of semiconductor devices to smaller and smaller sizes has imposed a much more stringent requirement on the sensitivity of wafer or photomask inspection instruments which are called upon to detect contaminant particles and pattern defects as well as defects of the surfaces that are small compared to the size of the semiconductor devices. At the time of the filing of this application, design rule for devices of down to 0.13 microns or below has been in use or called for. At the same time, it is desirable for wafer inspection systems to provide an adequate throughput so that these systems can be used for in-line inspection to detect wafer and other defects.

One type of surface inspection system known as bright field illuminates a large area in a scheme sometimes known as flood illumination. High resolution images of illuminated areas of a surface are obtained from radiation reflected by the surface by means of two-dimensional imaging optics as the surface is scanned underneath the imaging optics. Such system requires significant time to image the entire surface of a photomask or semiconductor wafer because of the data rate required for imaging. For this reason, bright field inspection is typically used in back-of-the-line wafer processing systems, rather than in production.

In some bright field systems, radiation from a source is passed through a beam splitter towards the surface that is being imaged, and reflected radiation from the surface is passed through the beam splitter again before the reflected radiation is directed to a detector. Thus the radiation passes through the beam splitter twice between the source and the detector, so that the intensity of the radiation is much reduced upon reaching the detector. This greatly reduces the amount of photons originating from the source that reach the detector, and therefore reduces the sensitivity of bright field inspection. It is therefore desirable to provide an improved bright field system where such deficiencies are not present.

In another type of semiconductor inspection system known as a dark field system, instead of illuminating a large area of the surface inspected, the beam illuminates a small area or spot on the surface, where the spot is scanned across the surface. Instead of detecting reflected radiation, the detector is placed away from the specular reflection direction to detect scattered radiation. Hence if there is no anomaly on the surface, the image obtained from the detector will be totally dark. For this reason, such systems are known as dark field systems. The detector in dark field systems will provide an output only when one or more anomalies are present, in contrast to bright field systems. If the background wafer pattern is sparse or can be filtered out of the basic signal, the instantaneous pixel (inspection area) can be larger in dark field than in bright field while still maintaining the same detection signal capability and data rate is not as much a limitation for such systems. Dark field systems therefore typically have larger pixels and higher inspection throughput compared to bright field systems.

In one type of dark-field imaging, a laser spot is scanned rapidly across the wafer surface as the wafer moves beneath the scanning spot, and a signal-element detector receives the optical signal scattered from objects on the wafer surface. This signal is processed to produce a simulated two-dimensional image, which is then analyzed to locate and characterize wafer defects. Spot-scanning dark-field systems generally have higher inspection speed than bright-field systems, but with lower image resolution, and suffer some signal noise resulting from pattern on the wafer surface. Inspection throughput in dark-field systems, while generally higher than bright-field systems, is nonetheless limited by the rate at which the laser spot can be scanned.

The problems of scanned spot dark field systems are compounded when dark field systems are called upon to detect smaller and smaller defects. If the illuminated spot is large relative to the size of the defects to be detected, dark field systems will have low sensitivity since the background or noise signals may have significant amplitudes in relation to the amplitudes of the signals indicating anomalies within the spot. In order to detect smaller and smaller defects, it is, therefore, desirable to reduce the size of the illuminated area on the wafer surface. However, as the size of the illuminated area is reduced, throughput is usually also reduced. It is therefore desirable to provide a dark field system with adequate sensitivity but improved throughput.

While the above-described systems may be satisfactory for some applications, they can be inadequate or expensive for other applications. It is, therefore, desirable to provide an improved surface inspection system with improved sensitivity and performance at a lower cost that can be used for a wider range of applications.

SUMMARY OF THE INVENTION

This invention relates to embodiments that employ means to generate a line of illumination on a surface of a sample such as a wafer, incident either normal to the wafer or oblique to the wafer or both, and that collect radiation in collection angles normal to the wafer or at an angle to the wafer.

The angle of incidence of the illumination beam at the surface inspected may be defined by the angle between the beam and a line that passes through the beam and is normal to the surface inspected. Certain anomalies such as particles scatter more radiation in response to illumination beams at large angles of incidence than to beams at smaller angles of incidence. On the other hand, other types of anomalies such as scratches, shallow elevations or depressions are more sensitive to radiation directed to the surface at small angles of incidence. Therefore, in one embodiment of one aspect of the invention, the surface inspected is illuminated by two radiation beams directed to it at two different angles of incidence. A first beam at an oblique angle of incidence to the surface of a sample is focused by optics to a line on the surface, where the first beam and a direction that is through the first beam and is normal to the surface defines an incidence plane of the first beam. The line is substantially in focus along the length of the line and is substantially in the plane of incidence of the first beam. The second beam is focused at a second different incidence angle to an illuminated area of the surface. Since the two beams are directed to the surface at different angles of incidence, a wider variety of defects can be detected by the system.

Radiation scattered or reflected from the first line and/or illuminated area is collected and the radiation collected from a portion of the line and/or illuminated area is focused to a corresponding detector in the array. In other words, each portion of the line is imaged onto a corresponding detector in the array. Since the line has a small dimension across its width, the detection sensitivity of the system is enhanced in a direction transverse (e.g. perpendicular) to the line. Preferably the dimension of the detector in the direction along the line is also chosen to be small, so that the resulting resolution of the detection system is the result of the dimensions of the width of the line in one dimension and the size of the detector in the other dimension, so that the system can be designed to have high detection sensitivity. On the other hand, since an entire line area of the surface is illuminated simultaneously, the system has higher throughput compared to dark field systems where an illuminated spot is scanned across the surface.

In addition to the first beam, the surface is illuminated either simultaneously or sequentially by a second beam of radiation at a second incidence angle different from the first incidence angle to illuminate an illuminated area on the surface. Collection optics may be used to collect scattered or reflected radiation from both the first line and the illuminated area on the sample surface and focus a portion of the line and illuminated area to corresponding detector in one or more detector arrays. Common collection optics and common set(s) of detectors may be employed for collecting and detecting the scattered or reflected radiation from the surface of the sample originating from both beams, which reduces the cost of the system. Since the two beams are at different angles of incidence at the surface, a wider variety of defects of the surface may be detected. In some embodiments, radiation from the two beams may be detected substantially simultaneously or sequentially.

Where the second beam is directed to the surface in a direction normal to or close to the normal direction to the surface, the above described embodiment is particularly advantageous. The collection optics and detectors may be placed such that the system combines the advantages of bright field and dark field systems.

Furthermore, where the second beam also illuminates a second line or a narrow region on the sample surface, the performance would be superior to that of conventional bright field systems, since substantially all of the photons in the beam are focused to a small area so that the line or the narrow region is illuminated with much higher intensity, thereby increasing the sensitivity of detection. Furthermore, as in the case of the first line illuminated by the first oblique beam, the narrow width of the second line or narrow region can be utilized to increase the detection sensitivity without compromising throughput, for the same reasons as those explained above for the first line.

The detector array may be placed at various different locations for detection, such as in bright field imaging, dark field imaging, double dark field imaging or near angle dark field imaging configurations, all as defined below. In addition, additional detector arrays may be employed in combination with the first array to arrive at various different combinations of these configurations.

For certain applications, the detector array may be one-dimensional or form a single file. For other applications, it may be desirable to employ a two-dimensional detector array. Time delayed integration may be employed to increase the signal-to-noise ratio.

Preferably, the illumination beam or beams are polarized, such as where one or both beams contain separately identifiable S, P or circular polarization components. When the scattered or reflected radiation is imaged, it is possible to pass only S or P polarization states, or to pass all polarizations with respect to the inspected surface.

Where the surface inspected contains diffracting structures such as a regular pattern, for some applications, it may be desirable to employ filters that filter out one or more spatial frequencies simultaneously.

For certain applications requiring higher resolution, it may be desirable to employ shorter wavelengths, such as wavelengths in the ultraviolet or deep ultraviolet range. For such applications, it may be desirable to employ high repetition rate pulse (or even continuous wave) radiation, such as radiation that is pulsed at a frequency that exceeds about 10 MHz. In another embodiment according to another aspect of the invention, the inventors envision a bright field system where the illumination beam is reflected by means of a reflector having an elongated shape, where the reflector is located in a collection aperture of collection optics that collects the radiation that is reflected or scattered by the surface. The elongated reflector reflects and directs radiation to the inspected surface. Since the reflector has an elongated shape, it does not significantly obstruct the collection function of the collection aperture, so that the amount of photons that passes from the source to the detector after reflection by the surface is higher than that in conventional bright field systems using a beam splitter.

BRIEF DESCRIPTION OF THE DRAWINGS

FIG. 9 is a schematic diagram of surface inspection system to illustrate an embodiment of the invention.

FIG. 10 is a schematic front view of the surface inspected and the collection optics portion of FIG. 9.

FIGS. 11A and 11B are respectively the side and front views of some of the components of the system of FIG. 9 to illustrate in more detail the operation of the gray or bright field portion of the system.

FIG. 12 is a schematic front view of the surface inspected and the collection optics of the system of FIG. 9 to illustrate one implementation of the system where the two illumination lines overlap one another.

FIG. 13 is a schematic front view of the surface inspected and the collection optics of the system of FIG. 9 to illustrate the implementation of the system where the two illumination beams illuminate lines that are offset from one another on the surface inspected.

FIG. 14 is a schematic front view of the system of FIG. 9 to illustrate the resolution of the system along the X-axis.

FIG. 15 is a schematic field of a portion of the system of FIG. 9 and of the surface inspected to illustrate the resolution of the system along Y-axis.

FIG. 16 is a schematic front view of components of the system of FIG. 9 and of the surface inspected to illustrate one embodiment where radiation of a particular polarization or unpolarized radiation is collected and detected.

FIG. 17A is a schematic side view of components of the system of FIG. 9 to illustrate the Fourier lines and cell geometry on the surface inspected and Fourier filters for blocking the Fourier lines.

FIG. 17B is a schematic view of a repetitive pattern on the surface inspected and the preferred directions of the diffraction orders from the pattern used for illustrating the invention.

For simplicity in description, identical components are labeled by the same numerals in this application.

DETAILED DESCRIPTION OF THE EMBODIMENTS

Bright-field image capability may be defined as using illumination from within the collection cone of the imaging optics, including laser-illuminated bright-field imaging. Dark-field image capability may be defined as using illumination from outside the collection cone of the imaging optics but within a plane containing the illumination axis and the axis normal to the wafer surface. Double-dark-field image capability may be defined as using illumination from outside the collection cone of the imaging optics and an imaging axis (of the imaging optics) which lies outside a plane containing the illumination axis and the axis normal to the wafer surface. Near-angle-dark-field image capability may be defined as using illumination incident near to the collection cone of the imaging optics or within the collection cone of the imaging optics but with the specular reflection from the wafer surface blocked.

The description below in reference to FIGS. 1-8 is mostly taken from the Related Application.

Figure 1:
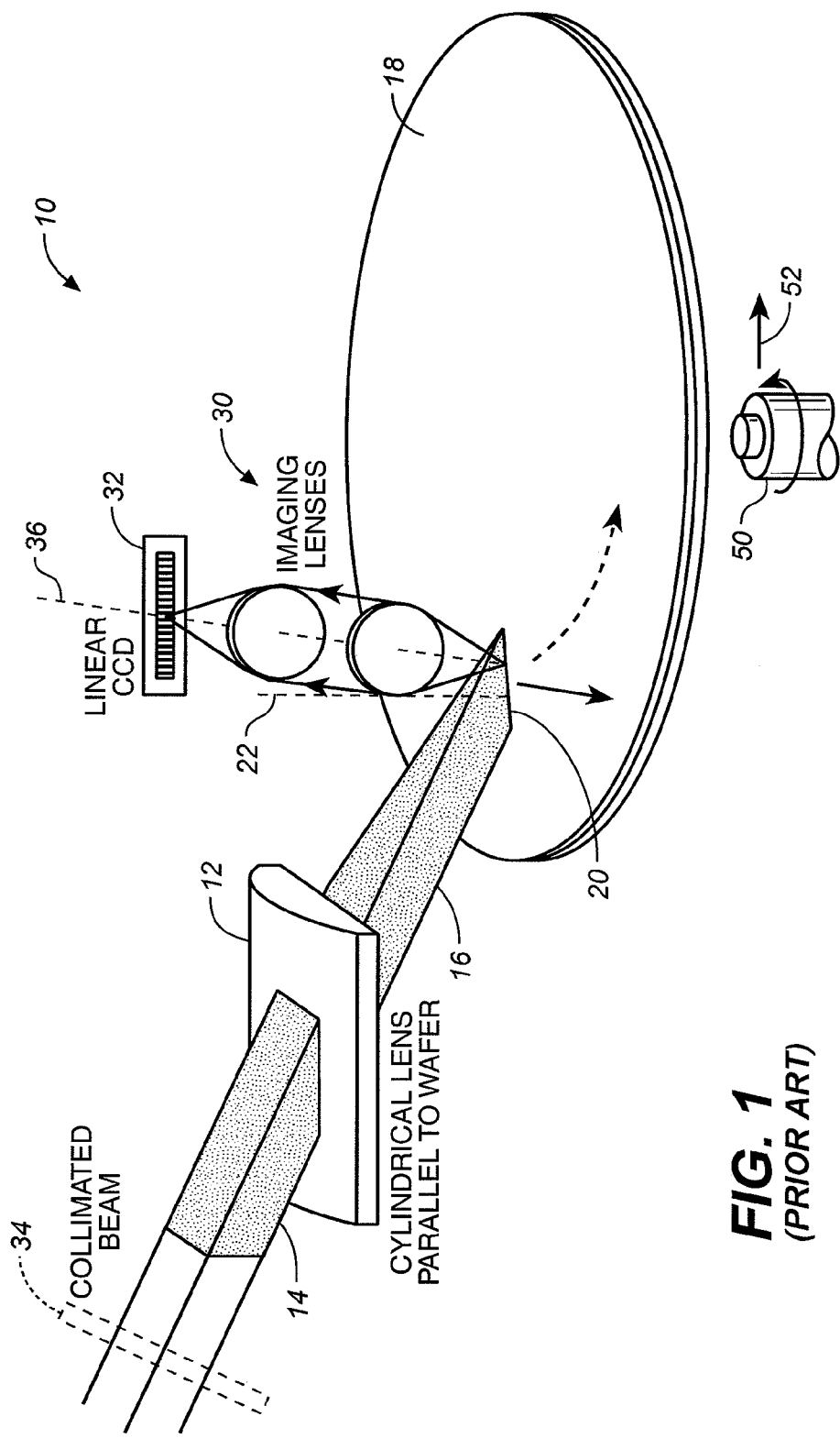
FIG. 1 is a perspective view of a surface inspection system to illustrate an embodiment of the Related Application.

FIG. 1 is a perspective view of a surface inspection system to illustrate the preferred embodiment of the invention of the Related Application. System 10 includes a cylindrical objective such as a cylindrical lens 12 for focusing a preferably collimated light beam 14 to a focused beam 16 for illuminating, on surface 18 to be inspected, an area in the shape of a line 20. Beam 14 and therefore also focused beam 16 are directed at an oblique angle of incidence to the surface 18. Line 20 is substantially in the incidence plane or plane of incidence of focused beam 16. In this context, the incidence plane of beam 16 is defined by the common plane containing beam 16 and a normal direction such as 22 to surface 18 and passing through beam 16. In order for the illuminated line 20 to be in the focal plane of lens 12 (that is, substantially all the points in line 20 are in focus with respect to lens 12), cylindrical lens 12 is oriented so that its principal plane is substantially parallel to surface 18. Image of the line is focused by an imaging subsystem 30 to an array of detectors, such as a linear array of CCDs 32. The linear array 32 is preferably parallel to line 20. The focusing power of lens 12 is applied only in the direction substantially normal to the incidence plane; in the other direction little or no focusing is applied by lens 12. Instead of using refractive lens 12, a reflective objective may be used instead; such and other variations are within the scope of the invention.

Figure 2:
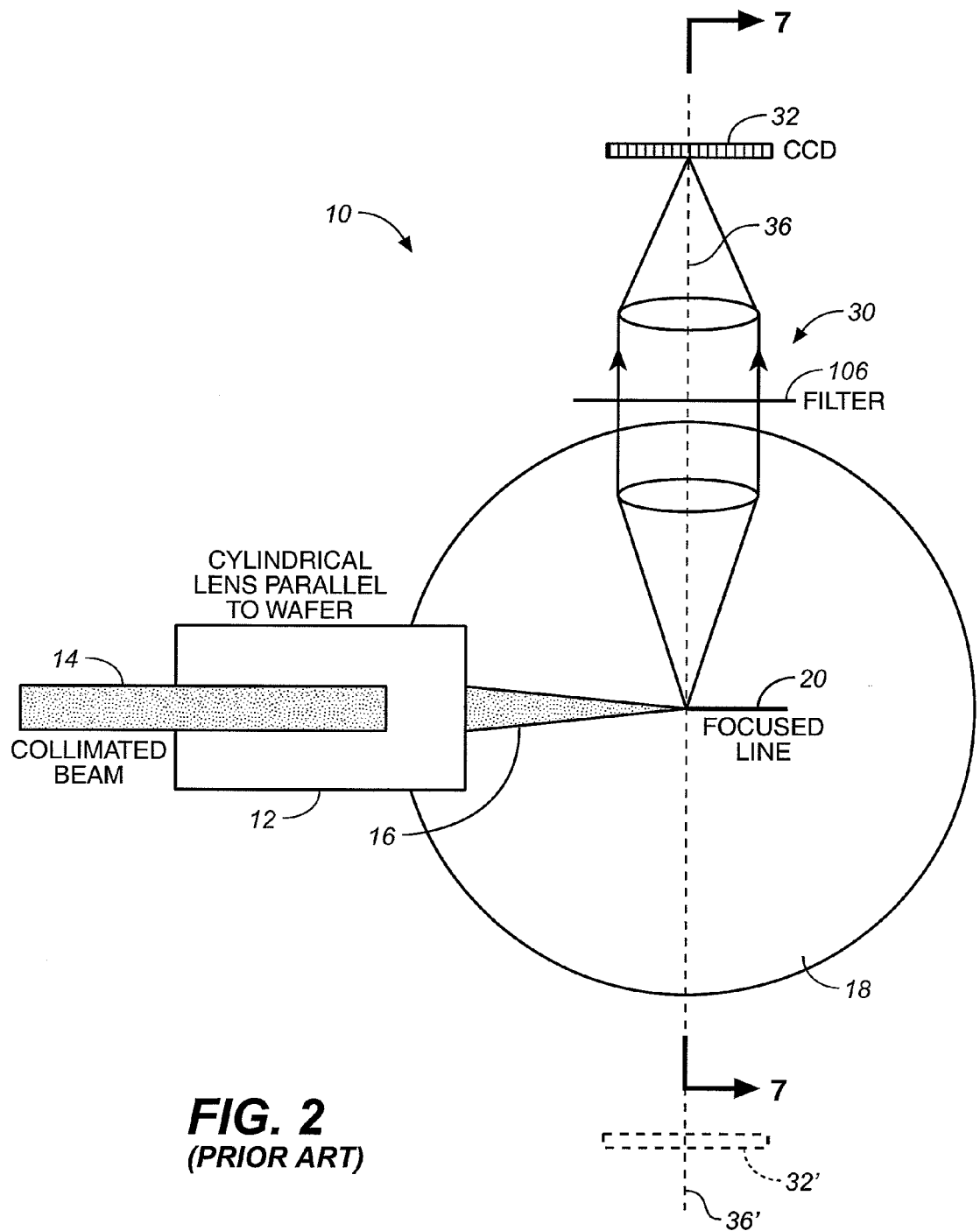
FIG. 2 is a top view of the system of FIG. 1.

In one embodiment particularly advantageous for detecting small size anomalies, the imaging subsystem 30 has an optical axis 36 which is substantially normal to line 20 so that the center portion of the linear CCD array 32 is in a plane substantially normal to the incidence plane of beam 16. The optical axis 36 may be oriented in any direction within such plane, including a position directly above the line 20, where array 32 would be in the plane of incidence of beam 16. In such event, array 32 would also be directly above line 20. If desired, another array 32' shown in dotted line in FIG. 2 may be placed in a position diametrically opposite to array 32, where array 32' has optical axis 36' also substantially normal to line 20. The two arrays together may be useful to detect 45 degree line patterns. It is to be noted that, even where arrays 32 and 32' are not in the plane of incidence of beam 16, in a configuration known as double dark field, substantially every portion of line 20 can still be at substantially the same distance from the corresponding detector in the array to which radiation from such portion is imaged by imaging optics. This means that imaging optics can be arranged (such as shown in FIG. 2) so that substantially all of the line 20 is within the focal plane of the imaging optics. In this manner, substantially all portions in line 20 can be imaged and detected at high sensitivity simultaneously.

The imaging subsystem 30 projects an image of a portion of the line 20 onto a corresponding detector in the CCD array 32 so that each detector in the array detects light from a corresponding portion of the line 20. The length of the line 20 is limited only by the size of the collimated input beam 14 and the physical aperture of lens or lens combination 12. In order to control the length of line 20, an optional expander 34 shown in dotted lines may be used for controlling the diameter of beam 14 so as to control the length of line 20.

Figure 3:
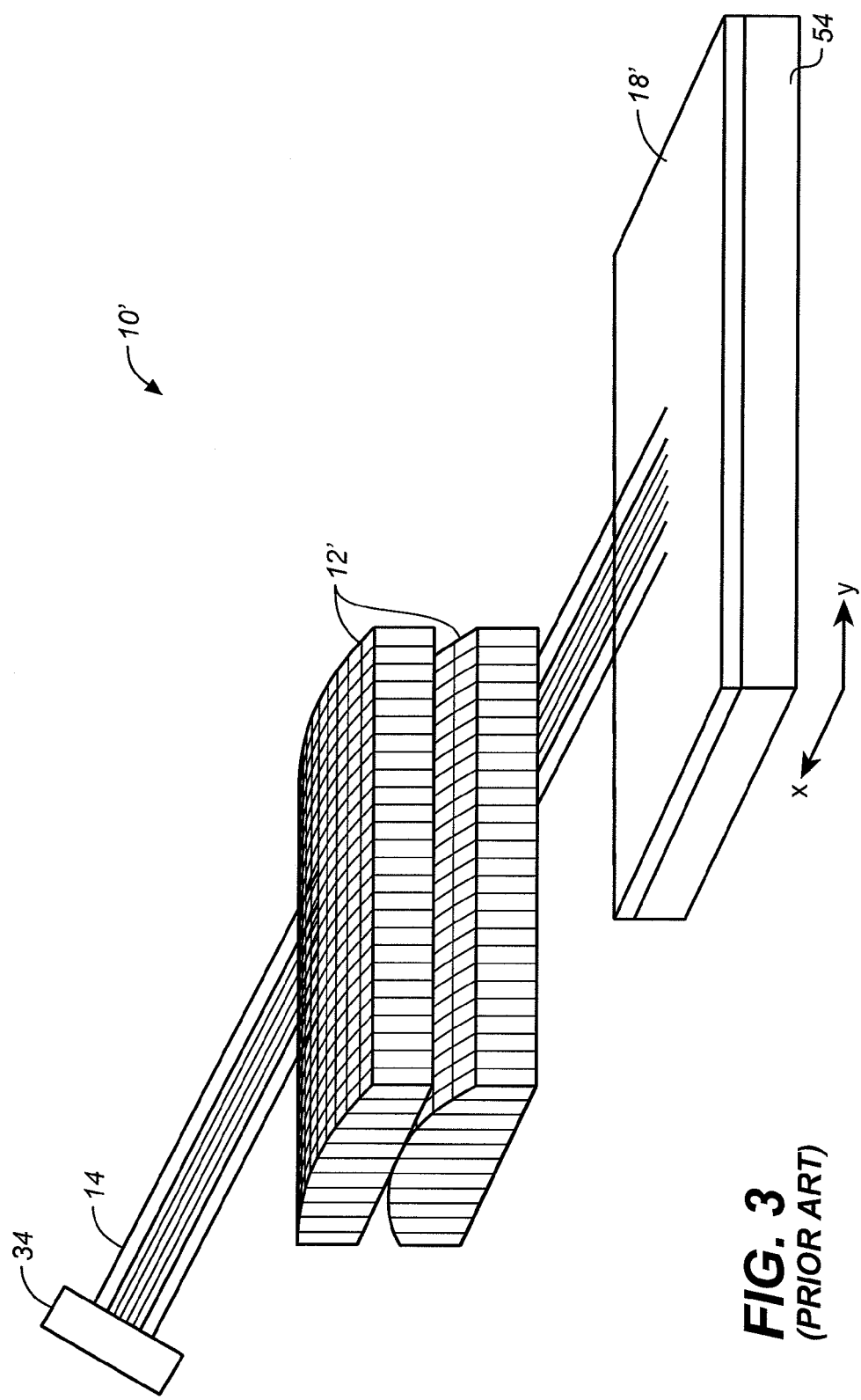
FIG. 3 is a perspective view of the illumination portion of a surface inspection system to illustrate an alternative embodiment of the invention in the Related Application.

FIG. 3 is a perspective view of an illumination portion of a wafer inspection system to illustrate an alternative embodiment of the invention of the Related Application. To simplify the diagram, the portion of the system for collecting and projecting an image of the illuminated line onto a detector array has been omitted. Instead of using a single symmetrical lens, the embodiment in FIG. 3 employs two cylindrical lenses 12' for tighter focusing, that is, focusing to a thinner line. In FIG. 1, both the illumination and collection portions of system 10 are stationary and surface 18 is rotated about a spindle 50 which is also moved along direction 52 so that line 20 scans surface 18 in a spiral path to cover the entire surface. As shown in FIG. 3, the surface 18' to be inspected can also be moved by an XY stage 54 which moves the surface along the X and Y directions in order for line 20 to scan the entire surface. Again, the illumination and collection portions of system 10' of FIG. 3 remain stationary. This is advantageous since it simplifies the optical alignment in the system, due to the fact that there is substantially no relative motion between the illumination portion and the collection portion of the system.

Figure 4:
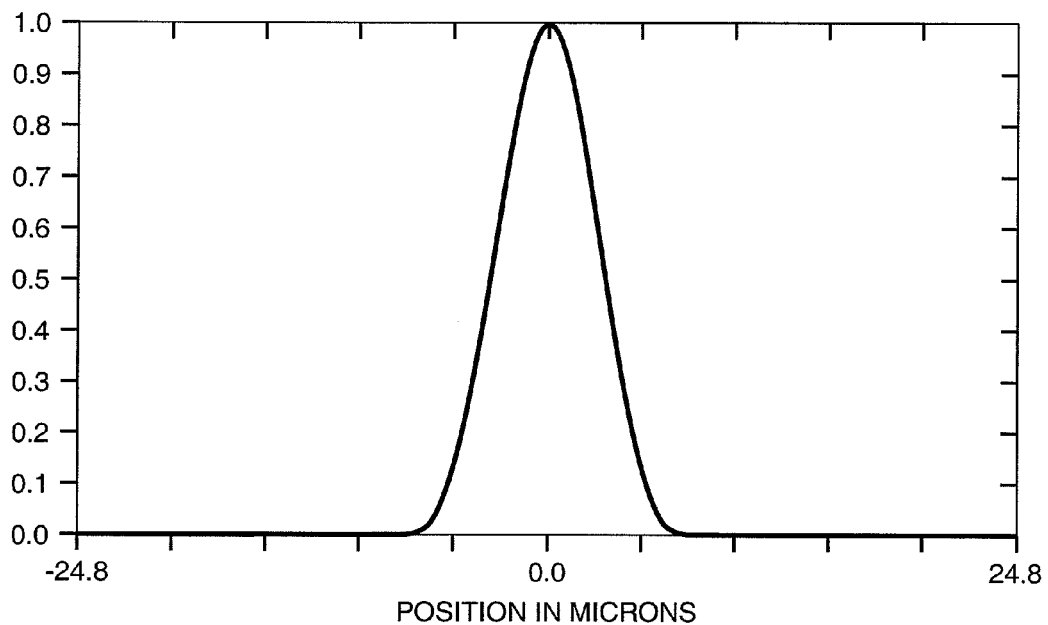
FIG. 4 is a graphical plot of a point spread function useful for illustrating the operation of the systems of FIGS. 1 and 3.

FIG. 4 is a graphical illustration of the point spread function of focused line 20 along the focused direction along any point of the line. As shown in FIG. 4, the point spread function of line 20 is Gaussian in shape, such as one which is produced if an 488 nm argon laser is used. Line 20 may also exhibit a varying point spread function along line 20 with a peak at the center of line 20. In order to avoid the variation of intensity along the line, it may be desirable to expand the beam by means of expander 34 to a longer length such as 10 or 11 mm and only use the center or central portion of the line, such as the central 3.3 or 5 mm of the line, so that power variation along the imaged portion of the line is insignificant. By means of an appropriate aperture in the imaging subsystem described below, it is possible to control the portion of the line imaged onto the array. As illustrated in FIG. 4, the point spread function of focused line 20 has substantially the same shape along the line, so that line 20 has a substantially uniform width.

Figure 5:
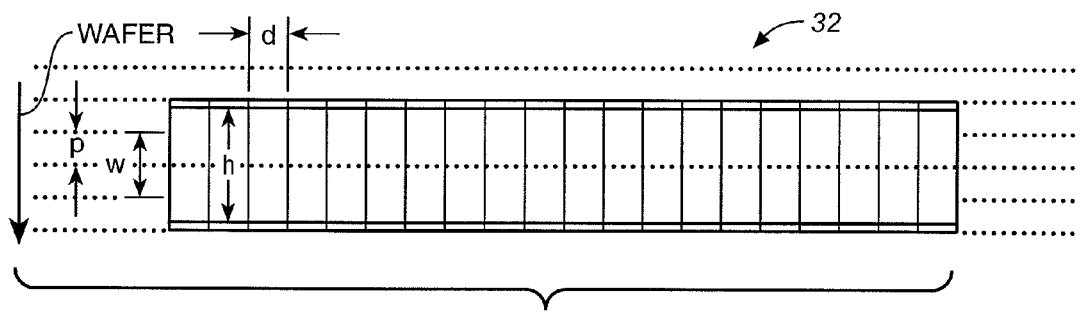
FIG. 5 is a schematic view of a parallel array of charged coupled devices (CCD) useful for illustrating the invention in the Related Application.

FIG. 5 is a schematic view of the linear CCD array 32. As shown in FIG. 5, the array 32 has dimension d in a direction parallel to the line 20, and W is the illumination line width. In other words, the image of line 20 as projected onto array 32 by subsystem 30 has a width of W. The pixel size of the inspection system 10 is determined by the scan pitch p and the pixel size of the detectors in the array 32 in a direction parallel to an image of line 20 on the detector array, or d. In other words, the pixel size is dp. Thus, assuming that the useful portion of the illumination line projected onto the CCD array 32 has a length of 5 mm, and the illumination line width W is 10 microns and array 32 has 500 elements with d equal to 10 microns and the scan line pitch is 5 microns, the effective pixel size on the wafer is 5 microns×10 microns, assuming that the image of the line at the array has the same length as the line. In practice, to avoid aliasing, at least two or three samples are taken in each direction (along line 20 and normal to it) per effective optical spot size on the sample surface. Preferably, reasonably high quality lenses such as quality camera lenses are used, such as ones having 5 mm field of view, giving a 30° collection angle.

From the above, it is seen that system 10 has high sensitivity, since the effective "pixel" size is 5×10 microns. At the same time, due to the fact that the whole line of pixels on the surface 18 are illuminated and detected at the same time instead of a single illuminated spot as in prior dark field systems, system 10 also has acceptable throughput. As noted above, the length of line 20 is limited only by the size of the collimated beam 14 and the physical aperture of lens or lens combination 12. Thus, assuming that the stage 54 has a stage speed of 10 microns per 0.1 millisecond, for a line scan rate of 10 kHz, the surface can be scanned at a speed of at least 50 mm per second, such as 100 mm per second. For a line 20 of 5 mm, the wafer surface is then scanned at a speed of 5 cm²/sec.

Figure 6:
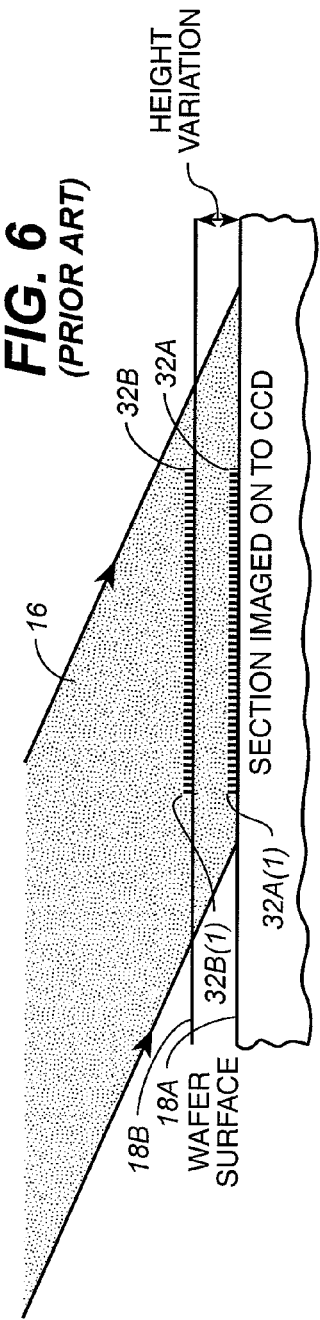
FIG. 6 is a schematic view of a light beam illuminating a line on a surface and corresponding positions of detectors of an array with respect to an imaging system along the line 6-6 in FIG. 2 to illustrate the operation of the system of FIGS. 1-3 in response to height variation of the surface inspected.
Figure 7:
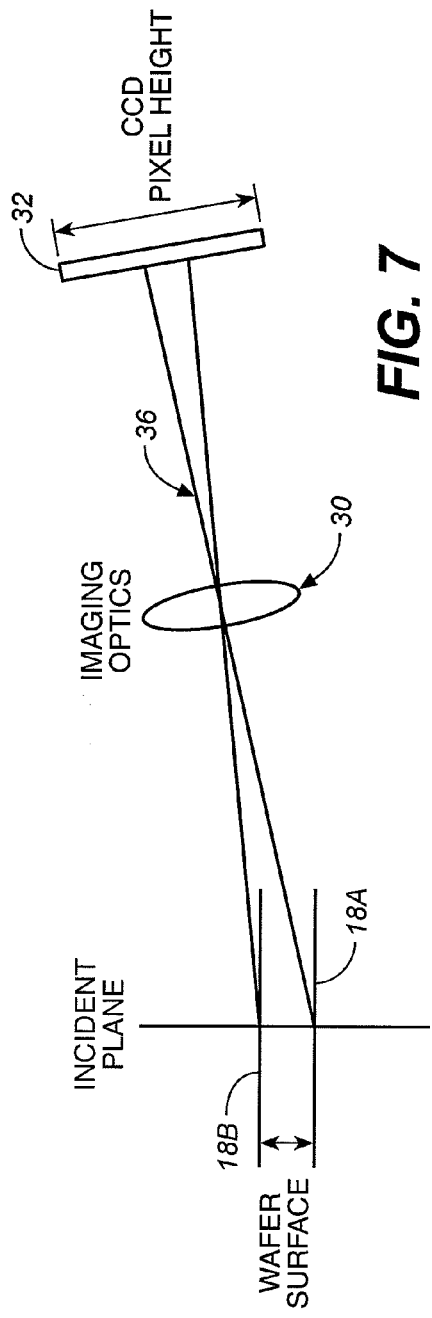
FIG. 7 is a schematic view of the imaging optics, the CCD detectors and a portion of the surface to be inspected of the system of FIG. 1 taken along the line 7-7 in FIG. 2 to illustrate the operation of the system of FIGS. 1-3 in response to height variation of the surface to illustrate the invention in the Related Application.

System 10 is also robust and tolerant of height variations and tilt of surface 18 and 18'. This is illustrated in reference to FIGS. 1, 2, 5-7. FIG. 6 is a cross-sectional view of a portion of the surface 18 in FIG. 2, focused beam 16 and two images of the array 32 when the surface 18 is at two different heights. FIG. 7 is a cross-sectional view of the CCD array 32, imaging subsystem 30 and two positions of a portion of the surface 18 to be inspected along the line 7-7 in FIG. 2.

In reference to FIGS. 1, 2 and 6, the imaging subsystem 30 will also project an image of the CCD array 32 onto surface 18 overlapping that of line 20. This is illustrated in FIG. 6. Thus, if surface 18 is in the position 18A, then imaging subsystem 30 will project an image 32A of the detector array on surface 18A, as shown in FIG. 6. But if the height of the surface is higher so that the surface is at 18B instead, then the imaging subsystem will project an image of the detector array at position 32B. The longer cross-sectional dimension of beam 16 is such that it illuminates both images 32A and 32B of the array.

From FIG. 6, it will be evident that the image of a particular detector in the array will be projected on the same portion of the surface 18 irrespective of the height of the surface. Thus, for example, the imaging subsystem 30 will project the first detector in the array 32 to position 32A(1) on surface 18A, but to the position 32B(1) on position 18B of the surface as shown in FIG. 6. The two images are one on top of the other so that there is no lateral shift between them. In the reverse imaging direction, an image of the same portion of surface 18 and, therefore, of line 20 will be focused to two different positions on the array 32, but the two positions will also be shifted only in the vertical direction but not laterally. Hence, if the detectors cover both positions, then the variation in height between 18A, 18B of the surface will have no effect on the detection by array 32 and the system 10, 10' is tolerant of vertical height variations of the surface inspected.

One way to ensure that the array 32 covers the images of line 20 on surface 18 at both positions 18A, 18B is to choose detectors in array 32 so that the dimension of the detectors in the vertical direction is long enough to cover such change in position of the surface, so that different positions of a portion of the line 20 will be focused by subsystem 30 onto the detector and not outside of it. In other words, if the vertical dimension of the detector is chosen so that it is greater than the expected height variation of the image of the line caused by height variation of the wafer surface, the change in wafer height will not affect detection. This is illustrated in more detail in FIG. 7.

As shown in FIG. 7, the pixel height (dimension normal to optical axis and line 20) of array 32 is greater than the change in position of the image of line 20 caused by a change in wafer surface height, so that the imaging optics of subsystem 30 will project the same portion of the surface and line on the wafer surface onto the same detector. Alternatively, if the pixel height of the CCD array 32 is smaller than the expected change in position of image of line 20 due to height variation in the wafer surface, multiple rows of CCDs may be employed arranged one on top of another in a two-dimensional array so that the total height of the number of rows in the vertical direction is greater than the expected height variation of the line 20 image. If this total height is greater than the expected movement of the image of the line in the vertical direction, then such two-dimensional array will be adequate for detecting the line despite height variations of the wafer surface. The signals recorded by the detectors in the same vertical column can be simply added to give the signal for a corresponding portion of the line 20.

Even if the height or vertical dimension of array 32 is smaller than the expected height variation of the wafer surface, the imaging optics of subsystem 30 may be designed so that the change in height or vertical dimension of the projected image of line 20 onto the CCD array is within the height of the CCD array. Such and other variations are possible. Thus, in order for system 10 and 10' to be tolerant of wafer height variation, the image of the line at the array 32 is longer than the array, and the extent of the height variations of the image of the line 20 on the detector array is such that the projected image still falls on the detector array.

Where a two-dimensional array of detectors is employed in array 32, time delayed integration may also be performed to improve signal-to-noise or background ratio, where the shifting of the signals between adjacent rows of detectors is synchronized with the scanning of the line 20 across surface 18.

Figure 8:
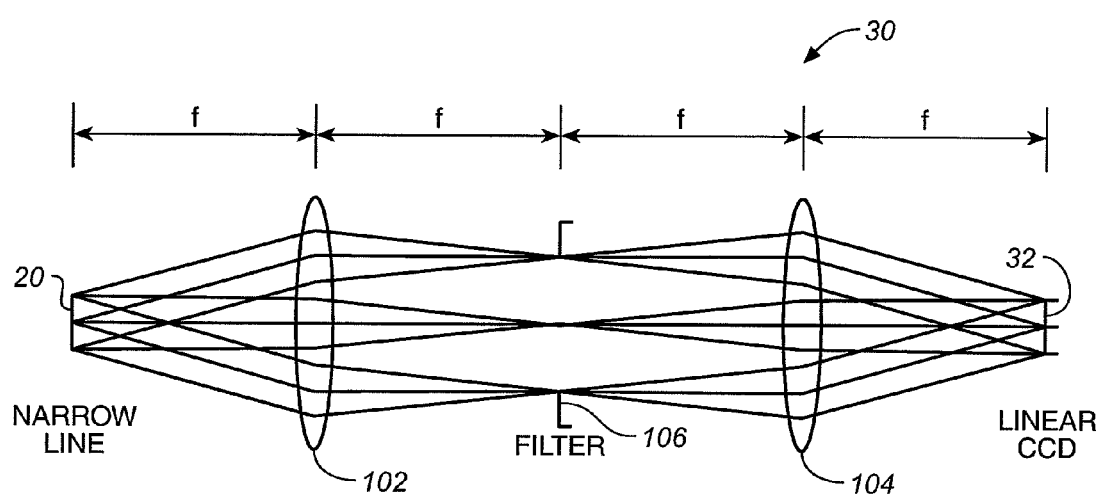
FIG. 8 is a schematic view of the collection and imaging optics in the system of FIG. 1.

FIG. 8 is a schematic view illustrating in more detail the imaging subsystem 30 of FIGS. 1 and 2. Subsystem 30 preferably comprises two lenses: lens 102 for collecting light from line 20 and to perform Fourier transform, and lens 104 for imaging the line onto the array 32. The two lenses 102, 104 preferably independently minimize aberration. Lens 104 will typically have a different focal length than lens 102 to magnify the length of the illumination line 20 to the actual scale of the sensor focal plane 32. A filter may be employed at position 106 commonly referred to as the Fourier plane of lens 102. A polarizer may be place at position 106 or between lens 104 and the focal plane (32 or 32'). The above description originates mostly from the Related Application.

FIG. 9 is a schematic view of a surface inspection system 200 to illustrate one embodiment of the invention. As shown in FIG. 9, an illumination beam is provided by a laser 202. The beam 204 from laser 202 is reflected by mirrors M1, to M2 and passes through one of three polarizers 206a, 206b, and 206c. An instrument such as a motor (not shown) is used to select one of the three polarizers to be placed in the optical path of beam 204. Polarizer 206a passes circular polarized radiation, polarizer 206b S-polarized radiation and polarized 206c P-polarized radiation. The polarized radiation is passed through waist relay zoom lenses and reflected by mirrors M3, M4 to a beam expander 210, which expands the beam in one direction for controlling a dimension of the area illuminated such as the width of line 20 (and of line 260 described below). A portion of the beam is then diverted by an oblique diverter 212, reflected by mirror M50 and M60 to a fixed beam expander 216 and is then focused by a cylindrical lens (or mirror) 12 to a line 20 on surface 18 that is being inspected. Expander 216 may be used to control a dimension of the beam 14 and of beam 16, such as their lengths.

Surface 18 is moved so that line 20 scans a spiral path, or moved along straight-line segments in the serpentine path along the X and Y-axis in the manner described above. In the embodiment of FIG. 9, the line 20 is aligned with the Y-axis, and the surface 18 is moved in a direction along the X-axis, so that line 20 scans a swath on surface 18. If the line scans a spiral path, then the swath is in the shape of a spiral. Where line 20 is scanned along a serpentine path, the swath covers rectangular strips of the surface, in a manner illustrated, for example, in U.S. Pat. No. 5,864,394 (e.g. FIG. 6). As will be noted from FIG. 9 beam 16 that is focused to a line on surface 18 is at an oblique angle to the surface 18. In one implementation, beam 16 is at an angle of about 65 degrees from a normal direction to surface 18. Obviously, the oblique beam 16 may be incident on surface 18 at other oblique angles away from the normal direction; such and other variations are within the scope of the invention.

Radiation scattered by surface 18 within the illuminated line 20 is collected and detected in up to three different collection and detection channels shown more clearly in FIG. 10. For simplicity and description, only one of the collection and detection channels is shown in FIG. 9, where the collection and detection channel collects and detects radiation scattered or reflected in a direction in or close to or adjacent to a normal direction to surface 18. This channel is referred to as the normal or near normal collection channel.

In the normal or near normal collection channel, an objective 222 collects radiation that is scattered by the illuminated line region 20. Preferably, objective 222 collimates the collected radiation and passes the collimated beam through two Fourier filters 224a and 224b, and several other objectives in the collection optics 230 to detector array 232. Similar to array 32, array 232 is aligned with line 20 (i.e. aligned along the Y-axis) so that radiation from each of the portions of line 20 is imaged by means of imaging optics to a corresponding detector in array 232. Such portions are substantially at the same distance from their corresponding detectors and within the focal plane of the imaging optics. All portions in line 20 may then be imaged and detected substantially simultaneously with high sensitivity. Auto focus capability may be provided by means of auto focus components 234. A beam splitter 236 diverts a portion of the collimated beam from objective 222 to components 234 for adjusting the position of surface 18 by means of a control system (not shown). Preferably objective 222 has a numerical aperture ("NA") of about 0.95, although objectives with NA of other values may also be used.

Where objective 222, optics 230 and array 232 are such that radiation collected and imaged onto array 232 is in a direction within the plane of incidence of beam 16, the subsystem formed by beam 16, objective 222 and optics 230 is in a dark field or single dark field configuration.

FIG. 10 illustrates the three collection channels in the system of FIG. 9. As shown in FIG. 10, in addition to the normal or near normal collection channel described above, two other channels with optics axes 36 and 36' illustrated in FIG. 2 may be employed to collect and detect radiation scattered in directions away from the plane of incidence of illumination beam 16. Since these two channels collect and detect radiation scattered in directions outside of the plane of incidence, these two collection channels are double dark field collection channels. The normal or near normal channel comprising objectives 222, 230 and detector array 232 collects and detects radiation scattered away from the specular reflection direction of beam 16. Where the radiation detected is within the plane of incidence of beam 16, the beam, objectives 222, 230 and array 232 form a dark field (sometimes known as single dark field) channel.

As described above, the stage and chuck cause relative motion between surface 18 and beam 16, such as by moving surface 18 preferably in a direction substantially perpendicular to line 20. Thus, in FIG. 10, surface 18 is moved along the X-axis. Surface 18 may also be moved in a direction transverse to but not perpendicular to line 20; such and other variations are within the scope of the invention. Preferably, the two double dark field collection and detection channels also employ Fourier filters (not shown in FIG. 10) similar to filters 224a and 224b shown in FIG. 9. Preferably, each of the Fourier filters employed in the three collection and detection channels comprises metal rods aligned in a direction perpendicular to the plane of incidence of the beam 16. The filters would block diffraction in the Y direction, such as diffraction from Manhattan geometry or from regular pattern such as memory arrays on semiconductor wafers.

In addition to the oblique illumination channel comprising beam 16 described above, the surface inspection system 200 also includes a second illumination beam. Thus the portion of radiation from beam 211 that is not diverted by diverter 212 is passed by the diverter to fixed beam expander 246 which further expands the beam 211 and the expanded beam is focused by a cylindrical objective 248 and reflected by a mirror 250 towards objective 222 which focuses the reflected radiation from mirror 250 as beam 252 towards surface 18 to illuminate another line region on surface 18. Expander 246 may be used to control a dimension of the beam 252, such as its length. The above illumination path is shown more clearly in reference to FIGS. 11A and 11B. The outputs of the detectors in arrays 32, 32' and 232 are supplied to a computer or processor 270 (in FIG. 9) for processing in order to detect anomalies on and/or in the surface inspected. Computer or processor 270 may also be used to control the spindle 50, stage 54 for moving the surface inspected, the auto focus components 234 for proper focusing, and the positioning of the polarizers. For simplicity, the connections between the computer or processor on one hand, and the arrays, auto focus components 234, motors for controlling polarizers on the other, are not shown in the figures. Where a circuit 280 (described below) is employed to perform time delayed integration of the outputs of the detectors 32, 32' and 232, computer or processor 270 may be used for controlling the circuit and for using the time delayed integrated signals for anomaly detection.

FIG. 11A is a side view of a portion of the system of FIG. 9 to illustrate the illumination and collection paths of radiation for the second illumination beam. FIGS. 11A and 9 are both side views of the system 200. As shown in FIG. 11A, the expanded beam from expander 246 is focused by a cylindrical lens (can be refractive or reflective) 248 to a beam having a cross section in the shape of a line. This beam is reflected by mirror 250 and focused by objective 222 to a line 260 on surface 18. The illumination line 260 is formed by a cylindrical objective 248 focusing an incoming illumination beam into beam 252 which is focused to a line at the Fourier plane of lens 222. Lens 222 then focuses this line to the actual illumination line 260 at the wafer. Note that in this imaging process, the direction of the illumination line at the Fourier plane 258 and the direction of the line 260 at the wafer are rotated by 90 degrees. A similar Fourier plane is located in the two side collection channels, such as one substantially at the location of filter 106 in FIG. 8.

Preferably, expander 210 may include two or more different objectives that can be selectively placed in the optical path of beam 204, so as to select a desired width of lines 20 and 260. The different objectives can be selectively placed by means of a linear slide or rotating wheel (not shown) controlled by means of a motor (not shown). Expander 210 can also include an objective that results in a wide beam 252 for flood illumination. While in the embodiment of FIG. 9, the same beam expander is used for controlling the widths of beams 16 and 252, it will be understood that different expanders may be used to control the widths of lines 20 and 260 separately and are within the scope of the invention.

FIG. 11B is a front view of a portion of system 200 of FIG. 9 to illustrate the illumination and collection paths of the second illumination beam. Line 260 may be imaged to detector arrays 32, 32' and 232 in a manner similar to line 20; line 260 is in the focal plane of imaging optics which includes lenses 222 and 248 (that is, substantially all the points in line 260 are in focus with respect to the imaging optics). The arrays 32, 32' and 232 are aligned with line 260 so that substantially all the points in line 260 are in the focal plane of the imaging optics imaging line 260 to the detector arrays.

The second illumination beam 252 is incident on surface 18 either in a normal direction to the surface or at a small angle to it (i.e. near normal direction), such as an angle which is less than 15 or 20 degrees from a normal direction to the surface. Preferably, such angle is less than 5 degrees, such as at about 1 degree. If detector array 232 is located to detect the specular reflection of beam 252, then beam 252 and the collection optics 222, 230 and detector array 232 form a bright field subsystem. If an obstruction (not shown) is located in the Fourier plane to block the specular reflection from line 260, collection optics 230, the obstruction, and the detector array 232 form a near angle dark field subsystem. As noted above, illumination from a normal or near normal direction is useful for detecting anomalies such as scratches and other anomalies, such as a shallow depression or gentle hill, or change in reflectivity of the surface. Different from conventional bright field designs employing beam splitters, a reflector having an elongated shape is used. In one embodiment, for example, a mirror 250 having a narrow width or a narrow partial reflecting mirror on a plate 250 is used instead as illustrated in FIG. 11A, so that it does not significantly (e.g. not more than half) obstruct the collection aperture of objective 230. The design illustrated in FIGS. 9, 11A and 11B therefore has a low sigma. In some implementations, sigma can range from 0.00001 to 0.5.

In the same vein, mirror 250 would not significantly obstruct the collection aperture of objective 230 when objective 230 and detector array 232 are used for detecting radiation scattered by line region 20 illuminated by oblique illumination beam 16. In this manner, the three collection and detection channels may be used for detecting radiation originating from both the oblique illumination beam 16 and the normal or near normal illumination beam 252 without having to use moving parts or otherwise moving the optical arrangement. The stage and chuck cause relative motion between surface 18 and beam 252, such as by moving surface 18 preferably in a direction substantially perpendicular to line 260. Surface 18 may also be moved in a direction transverse to but not perpendicular to line 260; such and other variations are within the scope of the invention.

With the above described optical arrangement, it is possible for the oblique illumination beam 16 and a normal or near normal illumination beam 252 to be employed sequentially to illuminate surface 18 and the same collection and detection apparatus may be used for detecting anomalies for both the illumination beams. Sequential scanning of course requires more time compared to where both beams are allowed to scan surface 18 simultaneously. Thus, to reduce the amount of time required for inspection, for some applications, it may be desirable for both beams to scan the surface simultaneously as illustrated in FIG. 12.

When both beams scan the surface simultaneously, the two illumination beams 16 and 252 may comprise radiation of different wavelengths, illuminating an overlapping line region 20, 260 shown in FIG. 12. The radiation collected by the three collection channels may then be separated by wavelengths. For example, the normal or near normal illumination beam 252 contains radiation of wavelength $\lambda 1$ and the oblique illumination beam 16 contains radiation of wavelength $\lambda 2$. For some applications, it may be adequate to use the two side channels for detecting radiation from the normal or near normal illumination beam 252 and use the normal or near normal detection channel for detecting radiation from the oblique illumination beam 16. In such circumstances, the optical arrangement illustrated in FIG. 12 will suffice.

As shown in FIG. 12, each detection channel is equipped with a pair of filters: 272a and 272b. In the two side detection channels with detector arrays 32, 32', the filters are aligned such that the filters 272a are in the optical path of the collected radiation to pass radiation wavelength λ1 to detectors 32 and 32' and blocks the passage of radiation of wavelength λ2. The filter pair in the normal or near normal channel is aligned such that filter 272b is in the optical path of the collected radiation to pass radiation of wavelength λ2 to detect array 232. Where radiation is to be separated by wavelength, two different radiation sources may be employed, one for supplying radiation for beam 16 and the other for supplying radiation for beam 252. Alternatively, if a radiation source can be found to supply radiation with both wavelengths, λ1 and λ2, the radiation may be filtered so that only radiation of length λ1 is passed to form beam 16 and only radiation of wavelength λ2 is passed to form beam 252. Such another variations are within the scope of the invention. Moreover, it is possible to alter the arrangement of the filters 272a and 272b so that radiation of wavelength λ1 from beam 252 is passed to array 232, and radiation of wavelength λ2 from beam 16 is passed to arrays 32 and 32'. Such variations are also within the scope of the invention.

Instead of separating the scattered or reflected radiation by means of wavelength, the two illumination lines 20 and 260 may also be separated by an offset when both beams illuminate the surface simultaneously. In such circumstances, the three collection and detection channels may be oriented to collect and detect from different lines at the same time, in an embodiment illustrated in FIG. 13. Thus, as shown in FIG. 13, the lines 20 and 260 are separated by an offset on surface 18. The optical axes 36 and 36' of the two side collection and detection channels (30, 32, 30', 32') are aligned to collect radiation scattered by surface 18 within the illuminated line region 20. Suitable apertures (not shown) may be used to block radiation from the adjacent line region 260 from reaching arrays 32 and 32' or the basic width limitation of the detector area can provide the line selection. The normal or near normal collection and detection channel (222, 230 and 232) is oriented to collect and detect radiation scattered or reflected by surface 18 within the line region 260. Suitable apertures (not shown) may be used to block radiation from the adjacent line region 20 from reaching array 232 or the basic width limitation of the detector area can provide the line selection. In such manner, surface 18 may be illuminated simultaneously by both beams and the three collection and detection channels can be operated separately to detect simultaneously radiation scattered or reflected from the lines 20 and 260.

As explained above, line 20 has substantially the same or uniform point spread function along its length as illustrated in FIG. 4. Thus when the image of line 20 is projected onto a detector array such as array 32, 32' or 232, the collected radiation has substantially the same point spread function at the detector array, unless the point spread function has been altered by the presence of an anomaly. Thus, as illustrated in FIG. 14, line 20 is aligned along the Y-axis and the array 232 (as well as arrays 32 and 32') is aligned along the same axis. When an image of line 20 is projected onto detector array 232, for example, the point spread function 232' is shown to have a shape similar to that of line 20 in FIG. 4. The same is true for the images on arrays 32 and 32'. Therefore, as noted above in reference to FIG. 5, the pixel size of the inspection system such as systems 10 and 200 is determined by the scan pitch p and the dimension d of the detectors in the arrays 232, 32 and 32' in the direction parallel to line 20, although the detectors in the different arrays may have different dimensions. In other words, the pixel size is dp.

In reference to FIG. 5, the image of line 20 as projected onto the detector array 32 (and similarly for arrays 32' or 232) by system 200 has a width of W. However, as the line scans across the surface 18, more than one sample may be taken within the line region 20, as illustrated by the scan pitch p. Thus, if the scan pitch p is equal to half of W, this means that two samples are taken within the line width W. This is accomplished by sampling the outputs of the detector array when the image of line 20 is in one position and sampling the outputs again after the line has been moved by the distance p, which is equal to (½)W. This will result in reducing the pixel size in the swathing direction from W to (½)W. Hence, by focusing the radiation beam to a line on surface 18, it is possible to reduce the number of samples that need to be taken within the line region, while increasing the resolution and sensitivity for detection in the direction perpendicular to the line 20 without requiring a high data rate for sampling. From the above, it is noted that the detection resolution or sensitivity in the direction along the length of line 20 is determined by the dimension of the detectors in the array, such as d. Therefore, by choosing detectors of the appropriate dimensions along the length of the image of the line in the three arrays, the desired resolution can be achieved.

From the above, it will be observed that system 200 is particularly advantageous for surface inspection. It provides an oblique illumination beam and a second illumination beam preferably directed in a normal or near normal direction to the surface inspected. The same collection and detection optics may be used for detecting radiation from both illumination beams, either sequentially or simultaneously. In contrast to conventional designs, the pixel size of the detector arrays can be chosen to increase sensitivity without unduly increasing the data rate required or reducing throughput. Since an entire line is scanned across surface 18, a much larger area is inspected at the same time compared to conventional systems where a single illuminated spot is scanned across the surface.

FIG. 15 is a side view of a portion of the system 200 to illustrate the invention. As shown in FIG. 15, an image of line 20 or 260 is projected by objectives 222 and 230 to the detector array 232, where the radiation scattered or reflected from a portion of the line is projected onto a corresponding detector in array 232. Therefore, the resolution or sensitivity of detection in a direction along line 20 or 260 is determined by the dimension d of the detectors in array 232 as illustrated in FIG. 15. As noted above, the dimension of the detectors in the array 232 need not be the same as those in arrays 32 and 32'.

As described above, beams 16 and 252 may be polarized to optimize sensitivity in detection of particular types of anomalies on surface 18. For this purpose, each of the three collection channels may also include a polarizer for enhancing detection sensitivity for particular types of defects. As shown in FIG. 16, each of the three channels includes a polarizing element, which can selectively pass only S- or only P-polarized radiation, or pass all radiation irrespective of polarization state. As illustrated in FIG. 16, the three polarizing elements each comprises a polarizer 282a that passes only S-polarized radiation, a polarizer 282b that passes only P-polarized radiation, and an optical element 282c that passes radiation of all polarization. As shown in FIG. 16, the three elements 282 are positioned to pass P-polarized radiation. Obviously, the polarizers may be moved from the positions shown in FIG. 16 to pass S-polarized radiation, or radiation of all polarization. One possible instrumentation for the polarizing element 282 is by means of a rotating wheel (not shown) with three different polarizers 282a, 282b, and 282c therein. By rotating the wheel by means such as a motor (not shown), the appropriate polarizer may be placed in the optical path of the collected radiation. A second possible instrumentation would be a linear slide that positions the polarizers into the beam. Both instrumentations are included in this invention.

FIG. 17A is a schematic side view of a portion of system 200 to illustrate another aspect of one embodiment of the invention. Where a regular pattern such as Manhattan geometry or memory array is present on surface 18, such pattern would cause diffraction from the illumination beams. The different diffraction orders may be blocked by means of Fourier filters. Preferably, filters are used to block diffraction orders having one or more different spatial frequencies. This may, for example, be accomplished by means of metal rods, such as one or two arrays of metal rods 224a and 224b as shown in FIG. 9. In the event that two filters are used, the two filters preferably have different spatial frequencies. Obviously more than two filters may be employed, where the filters may all have different spatial frequencies. Arrays of N independent rods can block up to N distinct spatial frequencies. The N rods may be arranged in any desired manner to form up to N filters, each filter comprising one or more rods. Independent rod filters that allow arbitrary spacing are included in this invention. FIG. 17B is a schematic view illustrating the preferred directions of the different diffraction orders from a pattern on surface 18. For lower spatial frequencies (typically less than 1 repeat pattern per micron on the wafer), more than one of the rods in the array is needed to block all lines from the frequency. In this way, N independent rods will yield blocking for N or for fewer than N spatial frequencies.

In an alternative embodiment, a broadband source such as an arc lamp may be used to supply the radiation for the illumination beam or beams instead of a laser. In such event, the beam or beams may illuminate a larger region on the surface 18 rather than a line, since it may be difficult to focus radiation from a large source to a line without drastically reducing the intensity of the radiation available from the source. For example, radiation for beam 252 may be supplied by such a source and the optics including lenses 248 and objective 222 may focus the radiation to a region such as a rectangular region on surface 18 instead of a line. In such event, it may be desirable to employ a two dimensional detector array instead of a linear array of detectors in arrays 32, 32' and 232. Time delayed integration may then be applied by means of a control circuit 280 of FIGS. 11A and 11B to enhance signal-to-noise ratio (control lines from circuit 280 to detector array 232, not shown). Two dimensional detector arrays and time delayed integration may also be useful for certain applications where the beam or beams are focused to a line or lines and not rectangular regions. While in the embodiment of FIG. 9, all three detection channels are present, for some applications, fewer than three detection channels may be adequate. Thus for some applications, a single double dark field channel and a normal or near normal channel may be adequate. For still other applications, a single double dark field channel may be sufficient. As noted above, the normal or near normal channel may be arranged to be a bright field channel or a near angle dark field channel. All such combinations are within the scope of the invention. Fewer than and more than 3 channels are both included in the scope of this invention. For example, only one of the three channels may be adequate for some applications. For other applications, two of the three channels may be enough. For still other applications, more than three channels may be desirable.

To increase the resolution or sensitivity of the detection, ultraviolet or deep ultraviolet radiation may be used, such as radiation of wavelength 355 nanometers. One possible radiation source that may be used is a pulsed laser operating at a frequency of more than 75 MHz. with power of up to one watt. One suitable laser for such purpose is a tripled Nd:YV04 mode locked laser. Pulsed lasers pulsing at frequencies other than at 75 MHz may also be used, such as one pulsing in excess of about 10 MHz in frequency. The collection objectives in the three collection and detection channels have numerical apertures of about 0.35. The two side channels are preferably oriented with the optical axis 36 and 36' at about 45 degrees from a normal direction to surface 18. Filters 224a and 224b may each include up to eleven metal rods; these filters may be suitable for filtering cell sizes from 0.29 to 5.9 microns.

Arrays 32 and 32' and 232 may each be a 4096 element diode array with a data rate of 1200 MMPS. The collection optics have magnifications such that the pixel sizes of the diode array can have different pixel sizes such as pixel sizes of 0.32, 0.44, 0.62 microns in the imaging direction, or one within a range of about 0.3 to 0.7 microns.

Lines 20 and 260 may be focused to have different widths, such as 1.5, 3.0, and 4.25 microns, or one within a range of about 1 to 5 microns, where the width of the line may be defined by the distance between the points where the intensity falls below $1/e^2$ of the peak intensity. The outputs of the detector arrays are sampled about three times within the width of each line region to give pixel dimensions in the swathing direction of 0.5, 1.0, and 1.42 microns, or one within a range of about 0.4 to 1.5 microns.

In contrast to dark field systems where an illumination spot is scanned across the surface, since an entire line region is illuminated at a time by beam 16 (and by beam 252), the scanning speed need not be as high as spot scanning systems, while achieving satisfactory output. Thus system 200 can achieve maximum velocity of 450 mm per second of scanned speed or higher.

In some bright field schemes (as well as dark field schemes described above), images of a target and a reference area used as a template are compared to determine differences therebetween. The reference area can be another area in addition to the target area on the same surface that is inspected, or can be a stored reference image in computer or processor 270. These differences may indicate surface anomalies.

While the invention has been described above by reference to various embodiments, it will be understood that changes and modifications may be made without departing from the scope of the invention, which is to be defined only by the appended claims and their equivalents. Thus while the embodiments have been illustrated by reference to detecting anomalies on semiconductor samples, such as patterned or unpatterned semiconductor wafers, it will be understood that the same system is applicable to the detection of anomalies on other types of samples, such as rough films, and backsides of wafers, as well as photomasks, reticles, liquid crystal displays or other flat panel displays. All references mentioned herein are incorporated in their entireties.

What is claimed is:

1. An optical apparatus for detecting anomalies of a sample, comprising:

first optics focusing a beam of radiation into a first focused beam at an oblique first incidence angle to a first line focused on a surface of the sample, said first beam and a direction that is through the first beam and that is normal to the surface defining an incidence plane of the first beam, said first line being substantially in the plane of incidence of the first beam;

second optics focusing a beam of radiation into a second focused beam at a second incidence angle to an illuminated area on the surface of the sample, said second incidence angle being different from the first incidence angle;

a first array of detectors;

collection optics collecting scattered or reflected radiation from the first line and/or the illuminated area on the sample surface and originating from the first and/or second beam and focusing the collected radiation from a portion of the line and/or the illuminated area to a corresponding detector in the first array.

2. The apparatus of claim 1, further comprising an instrument causing relative motion between the first beam and the sample so that the first line and illuminated area are scanned across the surface of the sample in a direction transverse to the first line.

3. The apparatus of claim 2, wherein the relative motion between the first beam and the surface causes the first line to be scanned over the surface at a speed in excess of 50 mm per second.

4. The apparatus of claim 1, said first detector array being in a double dark field location with respect to the first beam.

5. The apparatus of claim 4, further comprising a second detector array, said collection optics collecting radiation from the first line and/or the illuminated area on the sample surface scattered or reflected in a direction substantially normal or adjacent to a normal direction to the surface and originating from the first and/or second beam, and focusing the collected scattered or reflected radiation from a portion of the line and/or the illuminated area to a corresponding detector in the second array.

6. The apparatus of claim 4, further comprising a second detector array, wherein said second array detects specular reflections of the second beam from the surface of the sample.

7. The apparatus of claim 4, further comprising a second detector array, said collection optics collecting radiation from the first line and/or the illuminated area on the sample surface scattered in directions away from specular reflection directions of the first and second beams from the surface, and focusing the collected scattered radiation from a portion of the line and/or the illuminated area to a corresponding detector in the second array.

8. The apparatus of claim 1, further comprising a second detector array, said first and second detector arrays being arranged in double dark field locations with respect to the first beam, said collection optics collecting scattered radiation from the first line and/or the illuminated area on the sample surface and originating from the first and/or second beam and focusing the collected scattered radiation from a portion of the line and/or the illuminated area to a corresponding detector in each of the two arrays.

9. The apparatus of claim 8, further comprising a third detector array, said collection optics collecting radiation from the first line and/or the illuminated area on the sample surface scattered in a direction substantially normal to or adjacent to a normal direction to the surface and originating from the first and/or second beam, and focusing the collected scattered radiation to said third detector array.

10. The apparatus of claim 8, further comprising a third detector array, wherein said third array detects specular reflections of the second beam from the surface of the sample.

11. The apparatus of claim 1, said collection optics collecting radiation from the first line and/or the illuminated area on the sample surface scattered or reflected in a direction substantially normal to or adjacent to a normal direction to the surface and originating from the first and/or second beam, and focusing the collected scattered radiation to said first detector array.

12. The apparatus of claim 11, said second incidence angle being substantially 0 degrees from a normal direction or within 20 degrees from a normal direction, so that said first detector array detects scattered radiation in a near angle dark field or bright field configuration.

13. The apparatus of claim 11, said second incidence angle being substantially 0 degrees from a normal direction or within 5 degrees from a normal direction, so that said first detector array detects scattered radiation in a near angle dark field or bright field configuration.

14. The apparatus of claim 1, wherein said first array detects specular reflections of the second beam from the surface of the sample.

15. The apparatus of claim 1, said collection optics collecting radiation from the first line and/or the illuminated area on the sample surface scattered in directions away from specular reflection directions of the first and second beams from the surface, and focusing the collected scattered radiation to said first detector array.

16. The apparatus of claim 1, said apparatus comprising a second array of detectors.

17. The apparatus of claim 16, said second optics focusing the second beam to a focused second line on the surface of the sample, and said collection optics imaging said first and/or second line onto the second array of detectors, each detector in the second array detecting radiation from a corresponding portion of the first and/or second line.

18. The apparatus of claim 17, wherein resolution of the apparatus in a direction along the first or second line is determined by size of the detectors in the first or second array in a direction along a length of an image of the first or second line at such array.

19. The apparatus of claim 17, said first and/or second detector array comprising a one or two dimensional array of detectors.

20. The apparatus of claim 19, said first and/or second detector array comprising a two dimensional array of detectors, said apparatus further comprising a circuit controlling time delayed integration of output signals of the detectors in the first and/or second array.

21. The apparatus of claim 1, said second optics focusing the second beam to a focused second line on the surface of the sample, and said collection optics imaging said first and/or second line onto the first array of detectors, each detector in the first array detecting radiation from a corresponding portion of the first and/or second line.

22. The apparatus of claim 21, further comprising an instrument causing relative motion between the second beam and the sample so that the second line is scanned across the surface of the sample in a direction transverse to the second line.

23. The apparatus of claim 22, wherein the relative motion between the second beam and the surface causes the second line to be scanned over the surface at a speed in excess of 50 mm per second.

24. The apparatus of claim 21, further comprising a device altering width of an image of the first or second line at said first or second detector array to control resolution of detection in a direction perpendicular to the first or second line.

25. The apparatus of claim 24, said device comprising a beam expander in an optical path of the first or second beam.

26. The apparatus of claim 25, said device selectively places one of a plurality of objectives in said optical path.

27. The apparatus of claim 21, wherein resolution of the apparatus in a direction along the first or second line is determined by size of the detectors in the first or second array in a direction along a length of an image of the first or second line at such array.

28. The apparatus of claim 21, said first and/or second detector array comprising a one or two dimensional array of detectors.

29. The apparatus of claim 28, said first and/or second detector array comprising a two dimensional array of detectors, said apparatus further comprising a circuit controlling time delayed integration of output signals of the detectors in the first and/or second array.

30. The apparatus of claim 1, said second beam illuminating a substantially rectangular illuminated area that is focused on the surface of the sample.

31. The apparatus of claim 30, said apparatus comprising a two dimensional second array of detectors, wherein resolution of the apparatus is determined by size of the detectors.

32. The apparatus of claim 31, further comprising a circuit controlling time delayed integration of output signals of the detectors in the array.

33. The apparatus of claim 1, said first and/or second beam is polarized.

34. The apparatus of claim 33, wherein said first and/or second beam comprises P-polarized or circularized polarized radiation, and the collection optics collects unpolarized radiation scattered or reflected by the surface.

35. The apparatus of claim 33, said collection optics comprising a polarizing element.

36. The apparatus of claim 35, wherein said polarizing element passes P-polarized, S-polarized or radiation of all polarizations.

37. The apparatus of claim 33, wherein said first and/or second beam comprises P-polarized, S-polarized or circularized polarized radiation.

38. The apparatus of claim 1, wherein said first and/or second beam comprises pulsed radiation and wherein the pulsed radiation comprises at least one ultraviolet or deep ultraviolet wavelength.

39. The apparatus of claim 38, said pulsed radiation being pulsed at a frequency that exceeds about 10 MHz.

40. The apparatus of claim 1, wherein said first and/or second beam comprises continuous wave radiation.

41. The apparatus of claim 1, wherein said first and second beams comprise respectively radiation of a first and a second wavelength different from each other, and wherein both beams are focused to the surface substantially simultaneously.

42. The apparatus of claim 41, said apparatus comprising at least two detector arrays, wherein said collection optics comprises a device separating the radiation scattered by the surface into radiation of the first wavelength and radiation of the second wavelength before the scattered radiation is supplied to the at least two detector arrays.

43. The apparatus of claim 1, wherein the beams are focused to the surface sequentially.

44. The apparatus of claim 1, further comprising an instrument causing relative motion between the first and/or second beam and the sample so that said first and/or second optics are stationary when the first and/or second beam are caused to scan the entire surface of the sample.

45. The apparatus of claim 1, wherein said first and second beams are focused to the surface substantially simultaneously so that the first line and the illuminated area are separated by an offset.

46. The apparatus of claim 45, wherein said second beam is focused to a focused line on the surface.

47. The apparatus of claim 45, further comprising a second detector array, said collection optics collecting radiation from the first line and focusing the collected radiation from a portion of the first line to a corresponding detector in the first array, and collecting radiation from the illuminated area and focusing the collected radiation from a portion of the illuminated area to a corresponding detector in the second array.

48. The apparatus of claim 47, said first detector array being in a double dark field location with respect to the first beam, and the second detector array detecting radiation scattered or reflected by the illuminated area in a direction substantially normal or near a normal direction to the surface.

49. The apparatus of claim 1, said first or second optics, or both optics, comprising a cylindrical lens or a cylindrical mirror.

50. The apparatus of claim 1, said first optics focusing the first beam substantially only in a direction normal to the plane of incidence.

51. The apparatus of claim 1, said first or second optics comprising a cylindrical lens that has a principal plane substantially parallel to the surface.

52. The apparatus of claim 1, said first optics comprising a cylindrical lens that has a principal plane substantially parallel to the surface, wherein said first optics focuses an input radiation beam directed at the cylindrical lens, said input beam being in a direction oblique to the surface and to the principal plane of the lens.

53. The apparatus of claim 1, said first optics comprising a cylindrical mirror that has two substantially straight edges, wherein a plane defined by the two edges is substantially parallel to the surface.

54. The apparatus of claim 1, said first array of detectors being a linear array substantially parallel to the line.

55. The method of claim 1, wherein said collection optics and/or said array are/is such that an image of said line falls onto said array of detectors despite changes in position of the surface.

56. The apparatus of claim 1, wherein a dimension of said first array and/or said collection optics cause/causes an image of said first line to fall onto said first array of detectors despite changes in position of the surface.

57. The apparatus of claim 1, wherein said first line has a substantially uniform width.

58. The apparatus of claim 1, said first optics focusing a collimated beam into the first focused beam.

59. The apparatus of claim 1, said first array comprising detectors having pixel sizes along a direction along an image of the first line on the first array in the range of about 0.3 to 0.7 microns.

60. The apparatus of claim 1, said first line having a width in the range of about 1 to 5 microns.

61. An optical apparatus for detecting anomalies of a sample, comprising:
first optics focusing a beam of radiation into a first focused beam at an oblique first incidence angle to a first line focused on a surface of the sample;
second optics focusing a beam of radiation into a second focused beam at a second incidence angle to illuminated area illuminated area on the surface of the sample, said second incidence angle being different from the first incidence angle;
first detector array;

collection optics collecting scattered radiation from the first line and/or the illuminated area on the sample surface and originating from the first and/or second beam and focusing the collected scattered radiation from a portion of the line and/or the illuminated area to a corresponding detector in the first array, said collection optics comprising a spatial filter that filters the scattered radiation at one or more spatial frequencies.

62. The apparatus of claim 61, said first beam and a direction that is through the first beam and that is normal to the surface defining an incidence plane of the first beam, said first line being substantially in the plane of incidence of the first beam.

63. The apparatus of claim 61, said filter comprising a plurality of rods arranged in one or arrays at one or more spatial frequencies.

64. The apparatus of claim 63, wherein a two-dimensional diffracting structure is present on the surface of the sample, said one or more spatial frequencies of the filter match spatial frequencies of two-dimensional Fourier components from the two-dimensional structure on the surface of the sample.

65. The apparatus of claim 61, further comprising collection optics collecting scattered radiation from the first line and/or the illuminated area on the sample surface and originating from the first and/or second beam and focusing the collected scattered radiation from a portion of the line and/or the illuminated area to a corresponding detector in the first array.

66. The apparatus of claim 65, said collection optics collecting radiation from the first line and/or the illuminated area on the sample surface scattered in a direction substantially normal or adjacent to a normal direction to the surface and originating from the first and/or second beam, and focusing the collected scattered radiation from a portion of the line and/or the illuminated area to a corresponding detector in the first array.

67. The apparatus of claim 66, wherein said first array detects specular reflections of the second beam from the surface of the sample.

68. The apparatus of claim 66, said second incidence angle being substantially 0 degrees from a normal direction or within 15 degrees from a normal direction, so that said first detector array detects scattered radiation in a near angle dark field or bright field configuration.

69. The apparatus of claim 65, said collection optics collecting radiation from the first line and/or the illuminated area on the sample surface scattered in directions away from specular reflection directions of the first and second beams from the surface, and focusing the collected scattered radiation from a portion of the line and/or the illuminated area to a corresponding detector in the first array.

70. An optical apparatus for detecting anomalies of a sample, comprising:
first optics focusing a beam of radiation into a focused beam at an incidence angle to illuminated area illuminated area on the surface of the sample;
a first array of detectors;
collection optics collecting scattered radiation from the illuminated area on the sample surface and originating from the first beam and focusing the collected scattered radiation from a portion of the illuminated area to a corresponding detector in the first array,
wherein said optics comprises a reflector in a collection aperture of the collection optics that reflects the beam to the surface of the sample, said reflector having an elongated shape to reduce obstruction of the collection aperture of the collection optics.

71. The apparatus of claim 70, said beam being in a direction within a range of about 0 to 5 degrees from a normal direction to the surface of the sample.

72. The apparatus of claim 70, further comprising second optics focusing a beam of radiation into a second focused beam at an oblique second incidence angle to a line focused on a surface of the sample; said second incidence angle being different from the first incidence angle, said second beam and a direction that is through the second beam and that is normal to the surface defining an incidence plane of the second beam, said line being substantially in the plane of incidence of the second beam.

73. The apparatus of claim 70, said reflector comprising a narrow mirror or a narrow partial reflecting mirror on a plate.

74. The apparatus of claim 73, wherein a width of the narrow mirror is such that the mirror obscures not more than about half of a pupil of the collection optics.

75. The apparatus of claim 74, said illuminated area being in the shape of a rectangle or a line, said mirror having a width adequate for illuminating said rectangle or line.

76. The apparatus of claim 70, said collection optics collecting scattered or reflected radiation in a direction substantially normal to the surface of the sample from the illuminated area on the sample surface.

77. The apparatus of claim 76, said collection optics comprising an objective that focuses the first beam to a line on the surface, collects scattered or reflected radiation in a direction substantially normal to the surface of the sample from the line on the sample surface and focuses the collected scattered or reflected radiation from a portion of the line to a corresponding detector in the first array.

78. The apparatus of claim 77, said objective having a numerical aperture of not more than 0.95.

79. An optical method for detecting anomalies of a sample, comprising: focusing a beam of radiation into a first focused beam at an oblique first incidence angle to a first line focused on a surface of the sample, said first beam and a direction that is through the first beam and that is normal to the surface defining an incidence plane of the first beam, said first line being substantially in the plane of incidence of the first beam;
focusing a beam of radiation into a second focused beam at a second incidence angle to an illuminated area on the surface of the sample, said second incidence angle being different from the first incidence angle; and
collecting scattered or reflected radiation from the first line and/or the illuminated area on the sample surface and originating from the first and/or second beam and focusing the collected radiation from a portion of the line and/or the illuminated area to a corresponding detector in a first array of detectors.

80. The method of claim 79, further comprising causing relative motion between the first beam and the sample so that the first line and illuminated area are scanned across the surface of the sample in a direction transverse to the first line.

81. The method of claim 80, wherein the relative motion between the first beam and the surface causes the first line to be scanned over the surface at a speed in excess of 50 mm per second.

82. The method of claim 79, further comprising locating said first detector array to detect radiation scattered from the surface in directions away from the plane of incidence of the first beam.

83. The method of claim 82, further comprising collecting radiation from the first line and/or the illuminated area on the sample surface scattered or reflected in a direction substantially normal or adjacent to a normal direction to the surface and originating from the first and/or second beam, and focusing such collected scattered or reflected radiation from a portion of the line and/or the illuminated area to a corresponding detector in a second array of detectors.

84. The method of claim 82, further comprising placing a second detector array to detect specular reflections of the second beam from the surface of the sample.

85. The method of claim 79, wherein said collecting collects radiation from the first line and/or the illuminated area on the sample surface scattered or reflected in a direction substantially normal to or adjacent to a normal direction to the surface and originating from the first and/or second beam, and said focusing focuses the collected scattered radiation to said first detector array.

86. The method of claim 85, said second incidence angle being substantially 0 degrees from a normal direction or within 20 degrees from a normal direction, so that said first detector array detects scattered radiation in a near angle dark field or bright field configuration.

87. The method of claim 85, said second incidence angle being substantially 0 degrees from a normal direction or within 5 degrees from a normal direction, so that said first detector array detects scattered radiation in a near angle dark field or bright field configuration.

88. The method of claim 79, wherein said first array is located to detect specular reflections of the second beam from the surface of the sample.

89. The method of claim 79, wherein said collecting collects radiation from the first line and/or the illuminated area on the sample surface scattered in directions away from specular reflection directions of the first and second beams from the surface, and said focusing focuses the collected scattered radiation to said first detector array.

90. The method of claim 89, wherein said focusing of the second beam focuses such beam to a focused second line on the surface of the sample, and said collecting and focusing scattered or reflected radiation from the first and/or the second line images said first and/or second line onto a second array of detectors, each detector in the second array detecting radiation from a corresponding portion of the first and/or second line.

91. The method of claim 90, wherein resolution of the method in a direction along the first or second line is determined by size of the detectors in the first or second array in a direction along a length of an image of the first or second line at such array.

92. The method of claim 90, said first and/or second detector array comprising a two dimensional array of detectors, said method further comprising performing time delayed integration of output signals of the detectors in the first and/or second array.

93. The method of claim 79, wherein said focusing of the second beam focuses such beam to a focused second line on the surface of the sample, and said collecting and focusing scattered or reflected radiation from the first and/or the second line images said first and/or second line onto the first array of detectors, each detector in the first array detecting radiation from a corresponding portion of the first and/or second line.

94. The method of claim 93, further comprising causing relative motion between the second beam and the sample so that the second line is scanned across the surface of the sample in a direction transverse to the second line.

95. The method of claim 94, wherein the relative motion between the second beam and the surface causes the second line to be scanned over the surface at a speed in excess of 50 mm per second.

96. The method of claim 93, further comprising altering width of an image of the first or second line at said first or second detector array to control resolution of detection in a direction perpendicular to the first or second line.

97. The method of claim 96, wherein said altering comprises expanding a dimension of the first or second beam.

98. The method of claim 97, wherein said altering comprises selectively places one of a plurality of objectives in an optical path of the first or second beam.

99. The method of claim 93, wherein resolution of the method in a direction along the first or second line is determined by size of the detectors in the first or second array in a direction along a length of an image of the first or second line at such array.

100. The method of claim 93, said first and/or second detector array comprising a two dimensional array of detectors, said method further comprising performing time delayed integration of output signals of the detectors in the first and/or second array.

101. The method of claim 79, said second beam illuminating a substantially rectangular illuminated area that is focused on the surface of the sample.

102. The method of claim 101, wherein said collecting and focusing focuses radiation from the rectangular illuminated area to a two dimensional second array of detectors, wherein resolution of the method is determined by size of the detectors in the second array.

103. The method of claim 102, further comprising controlling time delayed integration of output signals of the detectors in the second array.

104. The method of claim 79, further comprising causing said first and/or second beam to be polarized.

105. The method of claim 104, wherein said first and/or second beam comprises P-polarized or circularized polarized radiation, and the collecting collects unpolarized radiation scattered or reflected by the surface.

106. The method of claim 104, wherein said collecting comprises polarizing radiation from said first and/or second beam collected from the surface.

107. The method of claim 106, wherein said polarizing of the collected radiation passes P-polarized, S-polarized or radiation of all polarizations.

108. The method of claim 104, wherein said causing causes said first and/or second beam to comprise P-polarized, S-polarized or circularized polarized radiation.

109. The method of claim 79, further comprising supplying radiation for forming said first and/or second beam, wherein the radiation supplied comprises pulsed radiation and wherein the pulsed radiation comprises at least one ultraviolet or deep ultraviolet wavelength.

110. The method of claim 109, said pulsed radiation being pulsed at a frequency that exceeds about 10 MHz.

111. The method of claim 79, further comprising supplying radiation for forming said first and/or second beam, wherein the radiation supplied comprises continuous wave radiation.

112. The method of claim 79, further comprising supplying radiation for forming said first and/or second beam, wherein said first and second beams comprise respectively radiation of a first and a second wavelength different from each other, and wherein both beams are focused to the surface substantially simultaneously.

113. The method of claim 112, further comprising detecting separately and by means of at least two detector arrays the collected radiation at the first and second wavelengths.

114. The method of claim 113, further comprising separating the radiation scattered or reflected by the surface into radiation of the first wavelength and radiation of the second wavelength before the scattered radiation is supplied to the at least two detector arrays.

115. The method of claim 79, wherein the beams are focused to the surface sequentially.

116. The method of claim 79, wherein said first and second beams are focused to the surface substantially simultaneously so that the first line and the illuminated area are separated by an offset.

117. The method of claim 116, wherein said second beam is focused to a focused line on the surface.

118. The method of claim 116, wherein said collecting and focusing collect radiation from the first line and focus the collected radiation from a portion of the first line to a corresponding detector in the first array, and collect radiation from the illuminated area and focus the collected radiation from a portion of the illuminated area to a corresponding detector in a second array of detectors.

119. The method of claim 118, further comprising placing said first detector array being in a double dark field location with respect to the first beam, and the second detector array detecting radiation scattered or reflected by the illuminated area in a direction substantially normal or near a normal direction to the surface.

120. The method of claim 79, wherein said focusing of the first beam focuses substantially only in a direction normal to the plane of incidence.

121. The method of claim 79, wherein said focusing of the first or second beam comprises orienting a cylindrical lens that has a principal plane so that such principal plane is substantially parallel to the surface.

122. The method of claim 79, wherein said focusing of the first beam comprises directing an input radiation beam at the cylindrical lens in a direction oblique to the surface and to the principal plane of the lens.

123. The method of claim 79, further comprising orienting said first array of detectors so that it forms a linear array substantially parallel to the line.

124. The method of claim 79, wherein said collecting causes an image of said line to fall onto said array of detectors despite changes in position of the surface.

125. The method of claim 79, wherein said focusing of the first beam is such that the first line has a substantially uniform width.

126. The method of claim 79, wherein focusing of said first beam focuses a collimated beam into the first focused beam.

127. The method of claim 79, wherein said focusing of the first beam is such that said first line having a width in the range of about 1 to 5 microns.

128. An optical method for detecting anomalies of a sample, comprising:
focusing a beam of radiation into a first focused beam at an oblique first incidence angle to a first line focused on a surface of the sample;
focusing a beam of radiation into a second focused beam at an second incidence angle to illuminated area illuminated area on the surface of the sample, said second incidence angle being different from the first incidence angle; and
collecting scattered radiation from the first line and/or the illuminated area on the sample surface and originating from the first and/or second beam and focusing the collected scattered radiation from a portion of the line and/or the illuminated area to a corresponding detector in the first array, wherein said collecting comprises passing the collected radiation through a spatial filter that filters the scattered radiation at one or more spatial frequencies.

129. The method of claim 128, wherein a two-dimensional diffracting structure is present on the surface of the sample, said one or more spatial frequencies of the filter match spatial frequencies of two-dimensional Fourier components from the two-dimensional structure on the surface of the sample.

130. The method of claim 128, wherein said collecting and focusing collect scattered radiation from the first line and/or the illuminated area on the sample surface and originating from the first and/or second beam and focus the collected scattered radiation from a portion of the line and/or the illuminated area to a corresponding detector in the first array.

131. The method of claim 130, wherein said collecting and focusing collect radiation from the first line and/or the illuminated area on the sample surface scattered in a direction substantially normal or adjacent to a normal direction to the surface and originating from the first and/or second beam, and focus the collected scattered radiation from a portion of the line and/or the illuminated area to a corresponding detector in the first array.

132. The method of claim 131, wherein said collecting and focusing collect specular reflections of the second beam from the surface of the sample and focus the collected radiation to said first array.

133. The method of claim 131, said second incidence angle being substantially 0 degrees from a normal direction or within 15 degrees from a normal direction, so that said first detector array detects scattered radiation in a near angle dark field or bright field configuration.

134. An optical method for detecting anomalies of a sample, comprising:
focusing a beam of radiation into a focused beam at an incidence angle to illuminated area illuminated area on the surface of the sample;
collecting by means of collection optics scattered radiation from the illuminated area on the sample surface and originating from the first beam and focusing the collected scattered radiation from a portion of the illuminated area to a corresponding detector in a first array of detectors,
wherein said focusing employs a reflector in a collection aperture of the collection optics that reflects the beam to the surface of the sample, said reflector having an elongated shape to reduce obstruction of the collection aperture of the collection optics.

135. The method of claim 134, said beam being in a direction within a range of about 0 to 5 degrees from a normal direction to the surface of the sample.

136. The method of claim 134, further comprising focusing a beam of radiation into a second focused beam at an oblique second incidence angle to a line focused on a surface of the sample; said second incidence angle being different from the first incidence angle, said second beam and a direction that is through the second beam and that is normal to the surface defining an incidence plane of the second beam, said line being substantially in the plane of incidence of the second beam.

137. The method of claim 134, wherein a width of the reflector is such that the reflector obscures not more than about half of a pupil of the collection optics.

* * * * *